(12) United States Patent  
Potyrailo et al.

(10) Patent No.: US 10,060,872 B1
(45) Date of Patent: Aug. 28, 2018

(54) SENSING SYSTEM AND METHOD

(71) Applicant: General Electric Company, Schenectady, NY (US)

(72) Inventors: Radislav Alexandrovich Potyrailo, Niskayuna, NY (US); Pradheepram Ottikkutti, Lawrence Park, PA (US); Najeeb Kuzhiyil, McKinney, TX (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 11 days.

(21) Appl. No.: 15/431,382

(22) Filed: Feb. 13, 2017

(51) Int. Cl.
*F02D 41/00* (2006.01)
*G01N 27/12* (2006.01)
*F02D 41/26* (2006.01)

(52) U.S. Cl.
CPC ....... *G01N 27/125* (2013.01); *F02D 41/0027* (2013.01); *F02D 41/26* (2013.01); *F02D 2200/0611* (2013.01)

(58) Field of Classification Search
CPC ...... F02D 41/00; F02D 41/0027; F02D 41/26; F02D 2200/0611; G01N 27/12; G01N 27/125
See application file for complete search history.

(56) References Cited

U.S. PATENT DOCUMENTS

| 3,864,628 A | 2/1975 | Klass et al. | |
| 4,112,893 A * | 9/1978 | Anzai | F02D 41/1479 123/689 |
| 4,214,563 A * | 7/1980 | Hosaka | F02D 41/1455 123/687 |
| 4,237,829 A * | 12/1980 | Asano | F02D 41/1455 123/695 |
| 5,345,213 A | 9/1994 | Semancik et al. | |
| 6,095,651 A | 8/2000 | Kunt et al. | |

(Continued)

FOREIGN PATENT DOCUMENTS

EP 3040716 A1 7/2016

OTHER PUBLICATIONS

Consadori et al., "Algorithms to Improve the Selectivity of Thermally-Cycled Tin Oxide Gas Sensors", Sensors and Actuators, vol. 19, Issue 4, pp. 333-349, 1989.

(Continued)

*Primary Examiner* — Hieu T Vo
(74) *Attorney, Agent, or Firm* — GE Global Patent Operation; Pabitra Chakrabarti

(57) ABSTRACT

A system includes an impedance gas sensor configured to be in contact with one or more hydrocarbons. The impedance sensor includes electrodes and a sensing region circuit that is configured to have a sensing material and to generate electrical stimuli to the sensing material upon exposure to one or more hydrocarbons at one or more of a reduced heater voltage or a reduced sensing region temperature as compared to a prescribed heater voltage or a prescribed sensing region temperature. The system also includes one or more processors configured to receive electrical signals from the sensor, where the electrical signals are representative of impedance responses of the sensing material to one or more hydrocarbons. The one or more processors also are configured to analyze the impedance responses and determine an amount of at least one hydrocarbon of interest in the one or more hydrocarbons.

27 Claims, 13 Drawing Sheets

(56) References Cited

U.S. PATENT DOCUMENTS

| | | |
|---|---|---|
| 6,290,000 B1 | 9/2001 | Zamfes |
| 7,329,389 B2 | 2/2008 | Horovitz et al. |
| 7,523,653 B2* | 4/2009 | Smith .................. F02D 41/1446 |
| | | 73/114.69 |
| 7,911,345 B2 | 3/2011 | Potyrailo et al. |
| 8,475,716 B2 | 7/2013 | Potyrailo et al. |
| 9,052,263 B2 | 6/2015 | Potyrailo et al. |
| 9,217,810 B2 | 12/2015 | Bright |
| 9,312,713 B2 | 4/2016 | Graf et al. |
| 2007/0144236 A1 | 6/2007 | Stokes et al. |
| 2014/0208840 A1 | 7/2014 | Bright |
| 2016/0084985 A1 | 3/2016 | Bright |
| 2016/0187277 A1 | 6/2016 | Potyrailo et al. |

OTHER PUBLICATIONS

Göpel et al., "AC Measurements on Tin Oxide Sensors to Improve Selectivities and Sensitivities", Sensors and Actuators B: Chemical, vol. 26, Issues 1-3, pp. 13-18, 1995.

Yoshikawa et al., "Gas Sensing Based on a Nonlinear Response: Discrimination Between Hydrocarbons and Quantification of Individual Components in a Gas Mixture", Anal. Chem., vol. 68, Issue 13, pp. 2067-2072, 1996.

Everhart et al., "AC-Impedance-Based Chemical Sensors for Organic Solvent Vapours", Sensors and Actuators B: Chemical, vol. 36, Issues 1-3, pp. 363-369, 1996.

Persaud et al., "An Intelligent Gas Sensing System", Sensors and Actuators B: Chemical, vol. 44, Issues 1-3, pp. 512-516, 1997.

Kitora et al., "Temperature-Dependent Dynamic Response Enables the Qualification and Quantification of Gases by a Single Sensor", Sensors and Actuators B: Chemical, vol. 40, Issues 1, pp. 33-37, 1997.

Göpel et al., "Gas Identification by Modulating Temperatures of SnO2-Based Thick Film Sensors", Sensors and Actuators B: Chemical, vol. 43, Issues 1-3, pp. 45-51, 1997.

Reedy et al., "Temperature Modulation in Semiconductor Gas Sensing", Sensors and Actuators B: Chemical, vol. 60, Issues 1, pp. 35-42, 1999.

Powar et al., "Transient Response Analysis for Temperature-Modulated Chemoresistors", Sensors and Actuators B: Chemical, vol. 93, Issues 1, pp. 57-66, 2003.

Liu et al., "Gas Sensing Behavior of a Single Tin Dioxide Sensor Under Dynamic Temperature Modulation", Sensors and Actuators B: Chemical, vol. 99, Issues 2-3, pp. 444-450, 2004.

Wilkop et al., "Impedance Analysis of the Thickness Shear Mode Resonator for Organic Vapour Sensing", Sensors and Actuators B: Chemical, vol. 99, Issues 2-3, pp. 355-360, 2004.

Spetz et al., "Influence of Gate Bias of MISiC-FET Gas Sensor Device on the Sensing Properties", Sens. Actuators, B, vol. 108, pp. 501-507, 2005.

Perkins et al., "Capacitance and Conductance of Single-Walled Carbon Nanotubes in the Presence of Chemical Vapors", Nano Lett., vol. 5, Issues 12, pp. 2414-2417, 2005.

Maiti et al., "Selective Detection of Methane and Butane by Temperature Modulation in Iron Doped Tin Oxide Sensors", Sensors and Actuators B: Chemical, vol. 115, Issues 2, pp. 610-613, 2006.

Semancik et al., "The Potential for and Challenges of Detecting Chemical Hazards with Temperature-Programmed Microsensors", Sensors and Actuators B: Chemical, vol. 121, Issues 1, pp. 282-294, Jan. 30, 2007.

Wysocki et al., "Dual Interband Cascade Laser Based Trace-Gas Sensor for Environmental Monitoring", Optical Society of America, vol. 46, Issue 33, pp. 8202-8210, 2007.

Mirsky et al., "Combinatorial and High-Throughput Development of Sensing Materials: The First Ten Years", Chem. Rev., vol. 108, Issue 2, pp. 770-813, 2008.

Morris et al., "Position-Independent Chemical Quantitation with Passive 13.56-MHz Radio Frequency Identification (RFID) Sensors", Talanta, vol. 75, Issue 3, pp. 624-628, 2008.

Deng et al., "Selective Chemical Sensing Using Structurally Colored Core-Shell Colloidal Crystal Films", IEEE Sensors Journal, vol. 8, Issue 6, pp. 815-822, 2008.

Lindh et al., "RFID Sensors Based on Ubiquitous Passive 13.56-MHz RFID Tags and Complex Impedance Detection", Wireless Communication Mobile Computing, vol. 9, Issue 10, pp. 1318-1330, 2009.

Semancik et al., "Detecting Chemical Hazards with Temperature-Programmed Microsensors: Overcoming Complex Analytical Problems with Multidimensional Databases", Annu. Rev. Anal. Chem., vol. 2, pp. 463-484, 2009.

Burns et al., "Materials and Transducers Toward Selective Wireless Gas Sensing", Chem. Rev., vol. 111, Issue 11, pp. 7315-7354, 2011.

Koley et al., "Highly Sensitive and Multidimensional Detection of NO2 Using In2O3 Thin Films", Sensors and Actuators B: Chemical, vol. 160, Issue 1, pp. 251-259, Dec. 15, 2011.

Kummel et al., "Organic Thin-Film Transistors for Selective Hydrogen Peroxide and Organic Peroxide Vapor Detection", J. Phys. Chem. C, vol. 116, Issue 46, pp. 24566-24572, 2012.

Warner et al., "A Novel Composite Film for Detection and Molecular Weight Determination of Organic Vapors", J. Mater. Chem. C, vol. 22, pp. 13732-13741, 2012.

Amini et al., "A Breakthrough in Gas Diagnosis with a Temperature-Modulated Generic Metal Oxide Gas Sensor", Sensors and Actuators B: Chemical, vol. 166-167, pp. 419-425, May 2012.

Lin et al., "The High Sensitivity Gaseous Hydrocarbon Sensing Device Based on the Improved Signal Processing Circuit", International Conference on Optoelectronics and Microelectronics (ICOM), Aug. 23-25, 2012.

Zellers et al., "Vapor Discrimination by Dual-Laser Reflectance Sensing of a Single Functionalized Nanoparticle Film", Anal. Methods, vol. 5, pp. 4268-4272, 2013.

Riccobono et al., "Detection of Individual Vapors and Their Mixtures Using a Selectivity-Tunable Three-Dimensional Network of Plasmonic Nanoparticles", Angew. Chem. Int. Ed., vol. 52, Issue 39, pp. 10360-10364, Sep. 23, 2013.

Lei et al., "Pt-CeO2 Nanofibers Based High-Frequency Impedancemetric Gas Sensor for Selective CO and C3H8 Detection in High-Temperature Harsh Environment", Sensors and Actuators B: Chemical, vol. 188, pp. 1141-1147, Nov. 2013.

Haick et al., "Artificial Sensing Intelligence with Silicon Nanowires for Ultraselective Detection in the Gas Phase", Nano Lett., vol. 14, Issue 2, pp. 933-938, 2014.

Warner et al., "Rational Design of QCM-D Virtual Sensor Arrays Based on Film Thickness, Viscoelasticity, and Harmonics for Vapor Discrimination", Anal. Chem., vol. 87, Issue 10, pp. 5156-5166, 2015.

Andersson et al., "Discrimination and Quantification of Volatile Organic Compounds in the ppb-Range with Gas Sensitive SiC-FETs Using Multivariate Statistics", Sensors and Actuators B Chemical, vol. 214, pp. 225-233, 2015.

Zhong et al., "Towards Outperforming Conventional SSensor Arrays with Fabricated Individual Photonic Vapour Sensors Inspired by Morpho Bbutterflies", Nature Communications 6, 2015.

Xie et al., "A Novel Method in the Gas Identification by Using WO3 Gas Sensor Based on the Temperature-Programmed Technique", Sensors and Actuators B: Chemical, vol. 206, pp. 220-229, Jan. 2015.

Penlidis et al., "Novel Undercoupled Radio-Frequency (RF) Resonant Sensor for Gaseous Ethanol and Interferents Detection", Sensors and Actuators A: Physical 230, pp. 63-73, Jul. 1, 2015.

Dunbabin et al., "Quantifying Spatiotemporal Greenhouse Gas Emissions Using Autonomous Surface Vehicles", Journal of Field Robotics, Jul. 22, 2016.

Albertson et al., "A Mobile Sensing Approach for Regional Surveillance of Fugitive Methane Emissions in Oil and Gas Production", Environment Science Technology, vol. 50, Issue 5, pp. 2487-2497, 2016.

Radislav A. Potyrailo, "Multivariable Sensors for Ubiquitous Monitoring of Gases in the Era of Internet of Things and Industrial

(56) References Cited

OTHER PUBLICATIONS

Internet" Chemical Reviews, American Chemical Society, 2016. 116, pp. 11877-11923, 47 pages. GE Global Research. Niskayuna. NY, US.

* cited by examiner

SENSING SYSTEM AND METHOD

FIELD

One or more embodiments are disclosed that relate to systems and methods for sensing hydrocarbons.

BACKGROUND

Powered systems, such as vehicles, can be powered by consumption of hydrocarbon-based fuels. Some vehicles may consume natural gas to generate tractive effort and other electric power for propelling the vehicles. The propulsion systems of such vehicles may operate more efficiently (e.g., generate or produce more work per unit of fuel) when the natural gas supply to the propulsion systems includes or is formed from methane as opposed to other heavier hydrocarbons, such as ethane, butane, etc. Because the supply of natural gas to the propulsion systems may include impurities such as these heavier hydrocarbons, the vehicles may operate less efficiently at times. A need exists for a sensor that can detect the presence of one or more of these heavier hydrocarbons.

Conventional gas sensors for hydrocarbons, however, are non-selective devices exhibiting significant gas cross sensitivity and thus, low gas selectivity. For example, these sensors may not be able to differentiate between the desirable methane and less desirable, heavier hydrocarbons. The origin of this limitation of conventional sensors of being non-selective is in the conflicting requirements for sensor selectivity and sensor reversibility. The full and fast reversibility of sensor response is achieved via weak interactions between the analyte and a sensing film of the sensor, whereas the high selectivity of sensor response is achieved via strong interactions between the analyte gas and the sensing film.

BRIEF DESCRIPTION

In one embodiment, a system includes an impedance gas sensor configured to be in contact with one or more hydrocarbons. The impedance sensor includes electrodes and a sensing region circuit that is configured to have a sensing material and to generate electrical stimuli to the sensing material upon exposure to one or more hydrocarbons at one or more of a reduced heater voltage or a reduced sensing region temperature as compared to a prescribed heater voltage or a prescribed sensing region temperature. The system also includes one or more processors configured to receive electrical signals from the sensor, where the electrical signals are representative of impedance responses of the sensing material to one or more hydrocarbons. The one or more processors also are configured to analyze the impedance responses and determine an amount of at least one hydrocarbon of interest in the one or more hydrocarbons.

In one embodiment, a method includes placing an impedance gas sensor in contact with one or more hydrocarbons, applying (using a sensing region circuit and across electrodes of the impedance sensor) electrical stimuli to the sensing material upon exposure to one or more hydrocarbons at a reduced heater temperature, and analyzing electrical signals from the impedance sensor that are representative of impedance responses of the sensor to the electrical stimuli. The impedance responses are analyzed to determine an amount of a hydrocarbon of interest in the one or more hydrocarbons.

In one embodiment, a system includes an impedance sensor having a sensing film configured to be in contact with a fuel flowing to a dual fuel engine. The impedance sensor includes electrodes and a sensing region circuit that is configured to generate electrical stimuli across the sensing film. The system also includes one or more processors configured to receive electrical signals from the impedance sensor. The electrical signals are representative of impedance responses of the sensing film to the electrical stimuli. The one or more processors also are configured to analyze the impedance response and determine an amount of one or more of methane or ethane in the fuel based on the impedance responses.

DETAILED DESCRIPTION

One or more embodiments of the inventive subject matter described herein provide for sensing systems and methods that can sense and differentiate between different hydrocarbon-based components in a fuel or dispersed in ambient air. These sensing systems and methods may sense the presence and/or amount of methane and/or other, heavier hydrocarbons in a fuel supplied to a powered system, such as to a propulsion system (e.g., engine) of a vehicle. Also, these sensing systems and methods may sense the presence and/or amount of methane and/or other, heavier hydrocarbons in ambient air when emitted from different sources such as thermogenic or biogenic sources. The sensing systems and methods are unexpectedly sensitive to two or more different hydrocarbons relative to known sensing systems and methods while using only a single sensing device or sensor. Excitation conditions of the sensor are selected to provide selective quantitation of closely related gases, where the excitation conditions are a single level of operating voltage, a single level of operating temperature, and/or a single level of operating power.

Figure 1:
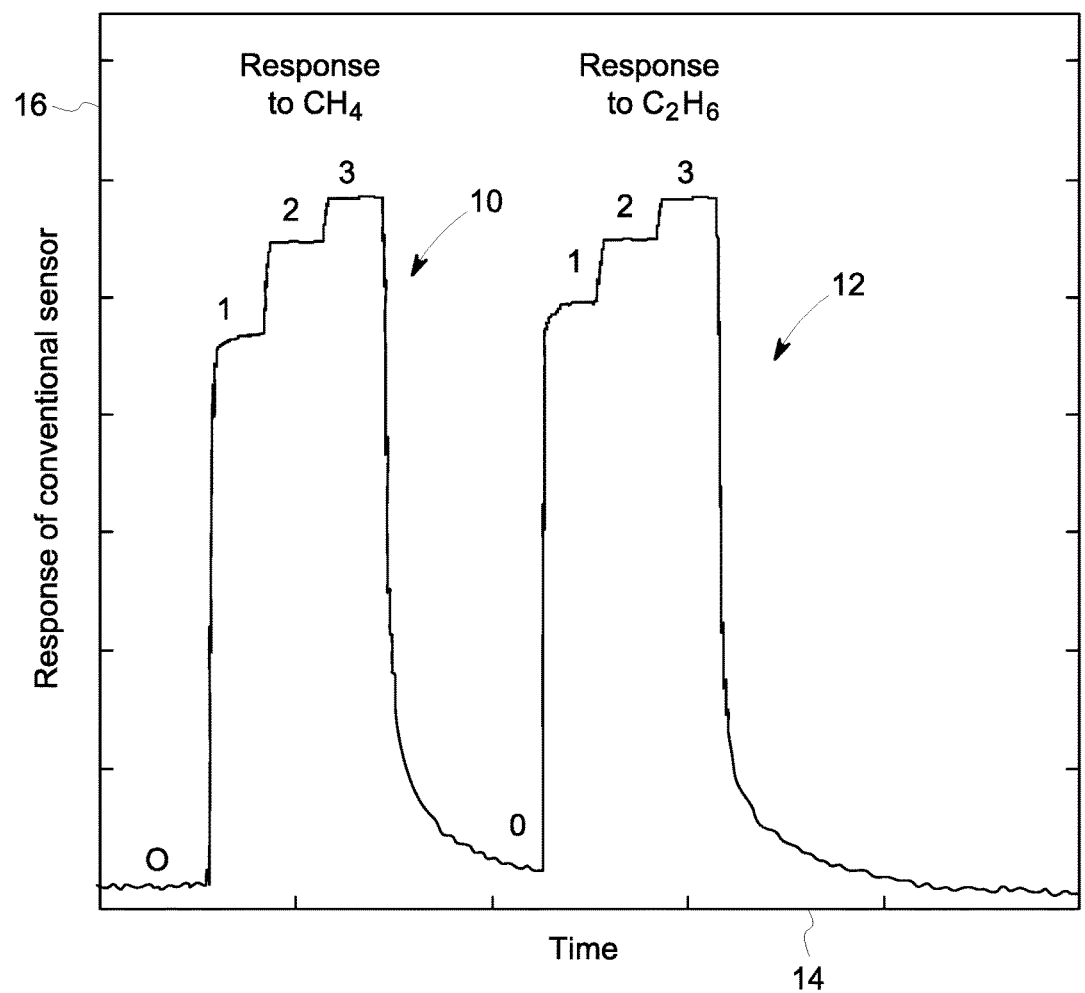
FIG. 1 illustrates responses of a sensor exposure to different hydrocarbons using the nominal prescribed operating conditions according to one example.

In one example, the sensor includes a metal oxide semiconductor material used for sensing hydrocarbon gases. As described herein, the sensing systems and methods may operate the sensors at operating conditions that are outside of the operating conditions prescribed for some known hydrocarbon sensors. For example, some known hydrocarbon sensors may operate by sensing resistance changes in a sensing material upon exposure to an environment containing hydrocarbon (e.g., gaseous or liquid hydrocarbon fuel) where the sensing material has a temperature that is modulated between a low temperature such as ambient room temperature of 20 degrees Celsius and elevated temperature of 300 degrees Celsius (or greater) and a hotter temperature, with a voltage (e.g., for a heater current) of several volts (for example one to five volts) applied to the heater of the sensor (to heat the sensing material or film). These operational settings or conditions may be prescribed by the manufacturer(s) of the sensors, and may be referred to as prescribed settings or conditions. Other operational settings or conditions may be prescribed by the manufacturer(s) of the sensors where there is a single level of a prescribed excitation setting or condition of operating voltage, a single level of operating temperature, and/or a single level of operating power But, these sensors may not be able to differentiate between different types of hydrocarbons. FIG. 1 illustrates responses 10, 12 of a conventional resistive sensor exposure to different hydrocarbons using the operating conditions prescribed above according to one example. The resistance responses 10, 12 are shown alongside a horizontal axis 14 representative of time and a vertical axis 16 representative of magnitudes of the sensor response. For example, the vertical axis 16 may represent resistances of the sensor. The response 10 represents the resistances measured by the sensor for methane and the response 12 represents the resistances measured by the sensor for the heavier ethane.

The sensor used to measure the responses 10, 12 has a metal oxide semiconductor sensing structure. This sensor has a tin oxide ($SnO_2$) semiconducting material that is required (per the manufacturer's instructions) to operate at 300 degrees Celsius to achieve the performance described by the manufacturer. Such a sensor gives a nonselective response to methane and other gases in ambient air when operated at this temperature, as provided by the voltage of a heater that should be five volts. In the performed experiments, different methane and ethane concentrations were used. As a non-limiting example, concentrations of methane and ethane were 0 parts per million (ppm), 56 ppm, 112 ppm, and 169 ppm, labeled as 0, 1, 2, and 3 in the responses 10, 12, respectively. Other concentrations of methane and ethane can be also detected. Under prescribed operation conditions of sensor heater voltage of five volts, as expected, the sensor did not discriminate between methane or ethane with measurements performed using resistance readout. As shown in FIG. 1, aside from the responses 10, 12 being measured at different times, the responses 10, 12 are nearly identical. For example, the responses 10, 12 have similar shapes with only slight differences. The small differences between the responses 10, 12 may prevent these responses 10, 12 from being useful for differentiating between the methane and ethane in a fluid (e.g., fuel or ambient air) under examination.

Figure 2:
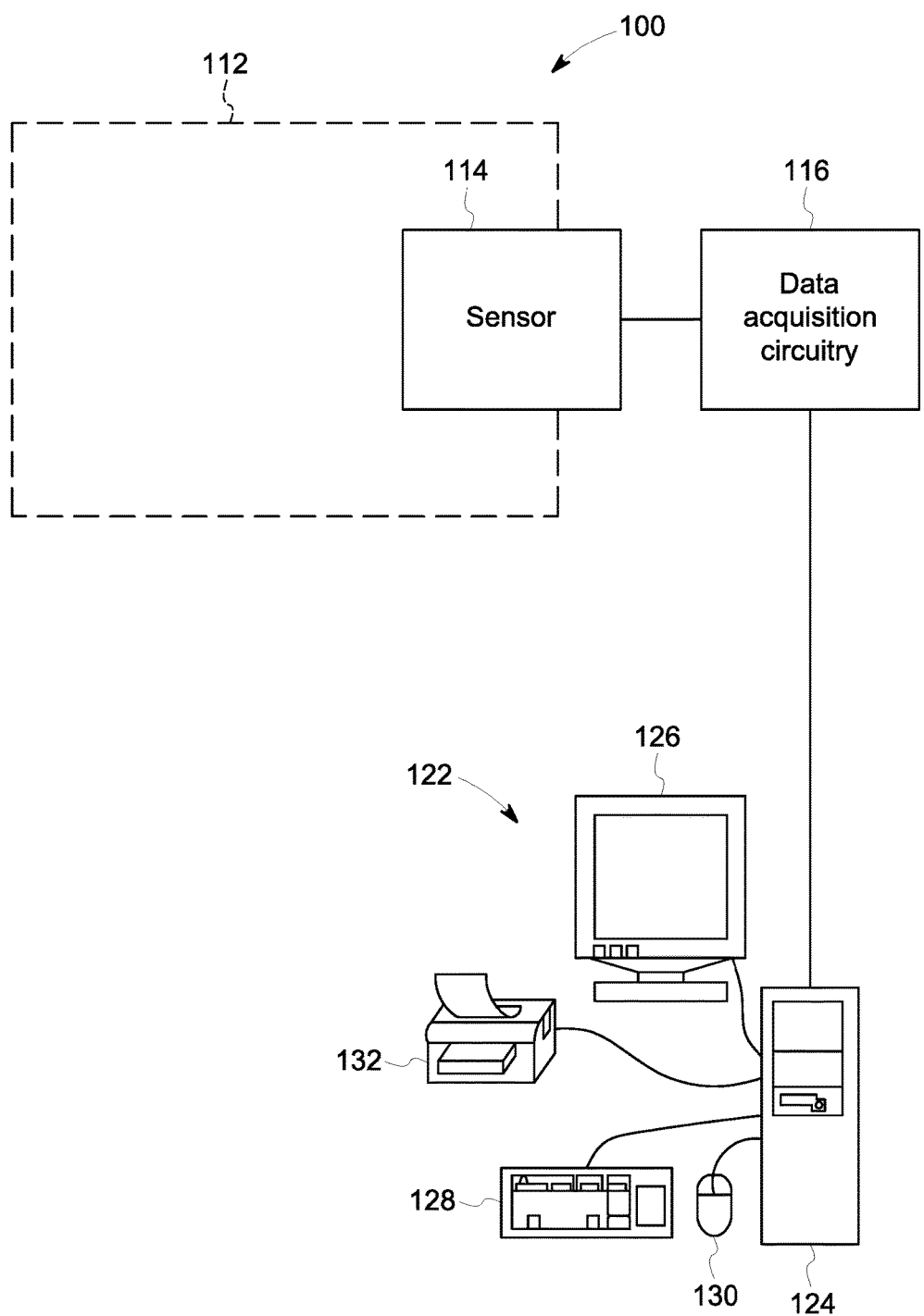
FIG. 2 illustrates one embodiment of a sensing system.

FIG. 2 illustrates one embodiment of a sensing system 100. The sensing system 100 examines a fluid in contact with the sensing system 100. This fluid may be fuel, such as a hydrocarbon-based fuel. One example of the fluid is natural gas that is supplied to a powered system (e.g., a vehicle, or a stationary generator set) for consumption. Other examples of such a fluid can include gasoline, diesel fuel, jet fuel or kerosene, bio-fuels, petrodiesel-biodiesel fuel blends, natural gas (liquid or compressed), and fuel oils. Another example of the fluid is ambient air. Another example of the fluid is ambient air with relatively small concentrations of hydrocarbons.

The system 100 may include a fluid reservoir 112 for holding the fluid and one sensor 114 at least partially disposed in, on, or within the fluid reservoir 112. Alternatively, the sensor 114 may be set in a flow path of the fluid outside of the reservoir 112, such as coupled to in-line connectors in fluid communication with the fluid reservoir that define a flow path. In one embodiment, the sensor 114 may provide continuous monitoring of the fluid within the reservoir or flow path.

The sensor 114 may detect characteristics or properties of the fluid via a resonant or non-resonant impedance spectral response. One or more of the inductor-capacitor-resistor resonant circuits (LCR resonators) may measure the resonant impedance spectral response. A non-resonant impedance spectral response is measured when the circuit does not contain an inductor. The resonant or non-resonant impedance spectrum of the sensor 114 in proximity to the fluid varies based on sample composition and/or components and/or temperature. The measured resonant or non-resonant impedance values Z' (which may be the real part of resonant impedance, Zre) and Z" (which may be the imaginary part of resonant impedance, Zim) reflect the response of the sensor to the fluid.

The electrical field may be applied to the sensing material or film of the sensor 114 via electrodes. The distance between the electrodes, may define the magnitude of the electric field applied to the sensor 114 (e.g., to the sensing material or film). The electrodes may be in direct contact with the sensing material. For example, a sensor 114 may be a combination of a sensing region and associated circuits. The sensing region is coated with the sensing material. The sensing material may be semiconductor material or metal oxide material.

Suitable sensors may include single use or multi-use sensors. A suitable multi-use sensor may be a re-usable sensor that may be used during the lifetime of a system in which it may be incorporated into. In one embodiment, the sensor may be a single use sensor that may be used during all or part of a reaction or process.

Data from the sensor 114 may be acquired via data acquisition circuitry 116, which may be associated with the sensor or which may be associated with a control system, such as a controller or workstation 122 including data processing circuitry, where additional processing and analysis may be performed. The controller or workstation may include one or more wireless or wired components, and may also communicate with the other components of the system. Suitable communication models include wireless or wired. At least one suitable wireless model includes radio frequency devices, such as radio frequency identification (RFID) wireless communications. Other wireless communication modalities may be used based on application specific parameters. For example, where there may be electromagnetic field (EMF) interference, certain modalities may work where others may not. The data acquisition circuitry optionally can be disposed within the sensor 114. Other suitable locations may include disposition being within the workstation. Further, the workstation can be replaced with a control system of the whole process where the sensor and its data acquisition circuitry may be connected to the control system of process.

The data acquisition circuitry may be in the form of a sensor reader, which may be configured to communicate wirelessly or wired with the fluid reservoir and/or the workstation. For example, the sensor reader may be a battery-operated device and/or may be powered using energy available from the main control system or by using harvesting of energy from ambient sources (light, vibration, heat, or electromagnetic energy).

Additionally, the data acquisition circuitry may receive data from one or more sensors 114 (e.g., multiple sensors positioned at different locations in or around the fluid reservoir). The data may be stored in short or long term memory storage devices, such as archiving communication systems, which may be located within or remote from the system and/or reconstructed and displayed for an operator, such as at the operator workstation. The sensors may be positioned on or in fuel or fluid reservoirs, associated piping components, connectors, flow-through components, and any other relevant process components. The sensors may be positioned outdoors or indoors for monitoring of thermogenic and biogenic emissions. The data acquisition circuitry may include one or more processors for analyzing the data received from the sensor 114. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed and/or stored in the hardware of the one or more processors.

In addition to displaying the data, the operator workstation may control the above-described operations and functions of the system. The operator workstation may include one or more processor-based components, such as general purpose or application-specific computers 124. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation or by associated components of the system. Alternatively, the programs and routines may be stored on a computer accessible storage and/or memory remote from the operator workstation but accessible by network and/or communication interfaces present on the computer. The computer may also comprise various input/output (I/O) interfaces, as well as various network or communication interfaces. The various I/O interfaces may allow communication with user interface devices, such as a display 126, keyboard 128, electronic mouse 130, and printer 132, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired.

Figure 3:
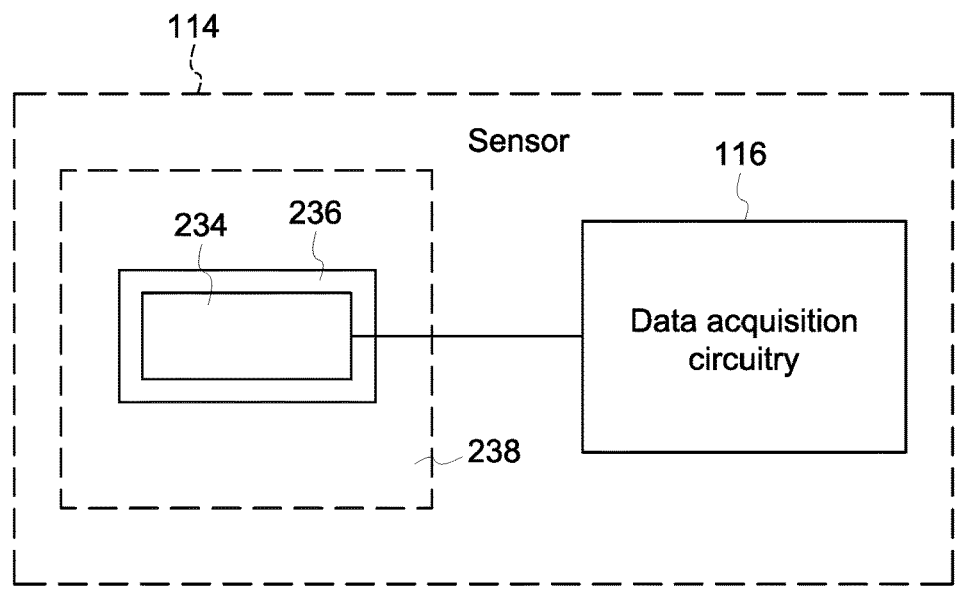
FIG. 3 illustrates a non-limiting example of a design of a sensor shown in FIG. 2.

FIG. 3 illustrates a non-limiting example of a design of the sensor 114. A sensing electrode structure 234 of the sensor may be connected to the data acquisition circuitry 116. The sensing electrode structure can be coated with a sensing coating 236. The sensing electrode structure, with the sensing coating, forms a sensing region 238. The sensing electrode structure, with the sensing coating that forms the sensing region, may operationally contact a fluid. The fluid contains the analyte or contaminant(s).

Suitable interdigital electrode structures for probing a fluid sample include two- and four-electrode structures. Suitable materials for electrodes include stainless steel, platinum, gold, noble metals, and others. Suitable materials of a substrate may include silicon dioxide, silicon nitride, alumina, ceramics, and others. Suitable examples of sensing materials or coatings include semiconducting materials, n-type semiconducting materials, p-type semiconducting materials, metal oxides, nanocomposites, or the like. Suitable electrodes may be formed using metal etching, screen-printing, ink-jet-printing, and mask-based metal deposition techniques. The thickness of fabricated electrodes on the substrates may be in the range from about 10 nanometers to about 1000 micrometers. The materials for the interdigital electrode structures, substrate, sensing layer, and electrode formation methods may be selected based at least in part on the application specific parameters.

Figure 4:
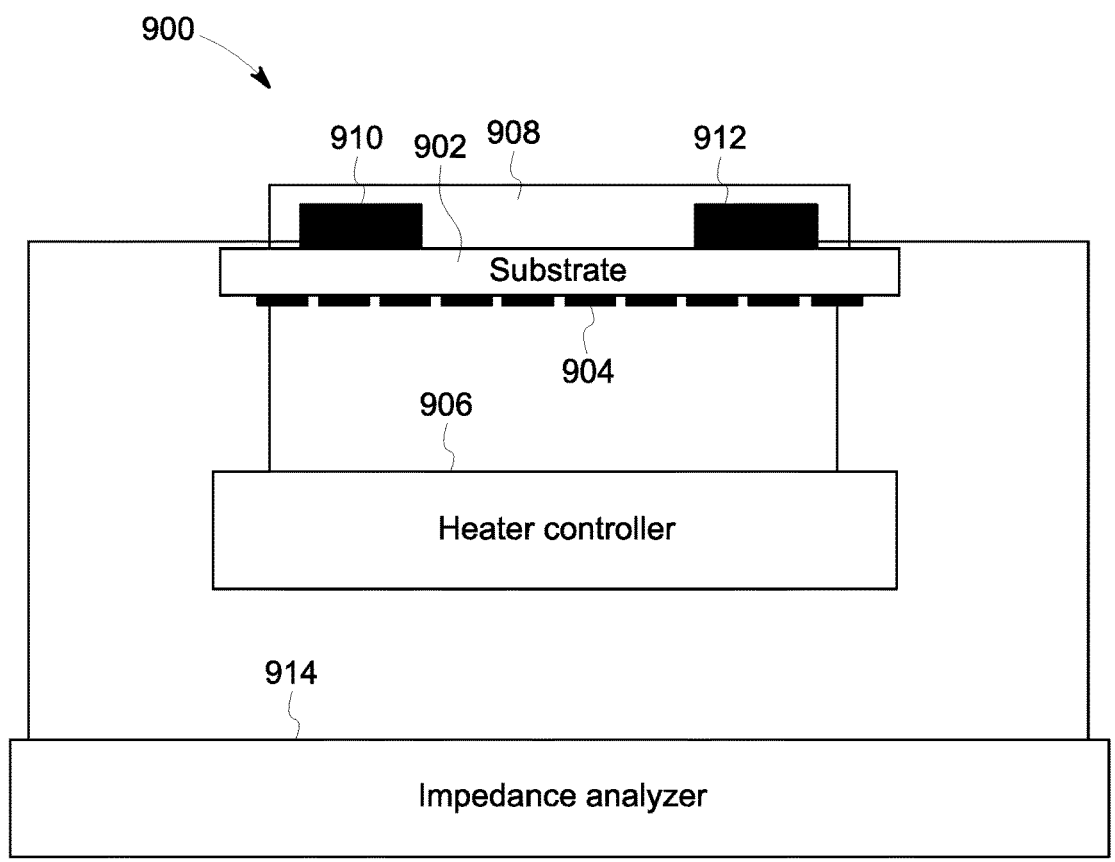
FIG. 4 illustrates one embodiment of a hydrocarbon sensor.

In one embodiment, the system may measure a impedance (f) (represented by Eq. (1)) of exposure of the sensing material or film of the sensor to a fluid sample while the sensing material or film is excited with electric stimuli and heated:

$$(f) = Z_{re}(f) + jZ_{im}(f) \qquad \text{Eq. (1)}$$

where $Z_{re}(f)$ may be the real part of the impedance and $Z_{im}(f)$ may be an imaginary part of the impedance. In one embodiment, the real part of the impedance $Z_{re}(f)$ and imaginary part of the impedance $Z_{im}(f)$ may be two components of a non-resonant impedance (f). In one embodiment, the real part of the impedance $Z_{re}(f)$ and imaginary part of the impedance $Z_{im}(f)$ may be two components of a resonant impedance (f). In one embodiment, the resonant impedance spectral response of the sensor may be a multivariable resonant response as more than one frequency may be utilized to measure sensor response across the resonance of the sensor. In some embodiments, the resonant impedance response of the sensor may be a multivariable resonant response because more than one frequency may be utilized to measure sensor response outside the resonance peak of the sensor. In some embodiments, the sensor response may be measured at multiple frequencies across the resonance of the sensor. For example, if the sensor with the electrodes coated with the sensing film resonates at about 10 MHz, the measured frequencies and associated sensor responses may be measured from about 8 MHz to about 12 MHz. This multivariable resonant response may be analyzed by multivariate analysis. The multivariable response of the sensing film of the sensor includes the sensor's full resonant impedance spectral response and/or several individually measured parameters, such as but not limited to $F_p$, $Z_p$, $F_z$, $F_1$, $F_2$, $Z_1$, and $Z_2$. As used herein, the term "resonant impedance spectral response" may be referred to as "impedance response," "multivariable resonant response," "resonant impedance spectra," and/or variations thereof FIG. 4 illustrates one embodiment of a hydrocarbon sensor 900. The sensor 900 may represent another version of the sensors or sensing systems described herein. The sensor 900 includes a substrate 902, such as a dielectric material. One or several heating elements 904, such as high resistance bodies, are coupled to one side of the substrate 902. The heating elements 904 receive electric current from a heater controller 906, which represents hardware circuitry that conducts the heater current or voltage to the heating elements 904 to heat the substrate 902 and to heat a sensing material or film 908 that is coupled to the other side of the substrate 902 and to electrodes 910 and 912. The sensing material 908 can include one or more materials deposited onto the substrate 902 to perform a function of predictably and reproducibly affecting the impedance sensor response upon interaction with the environment. For example, a metal oxide such as SnO2 may be deposited as the sensing material 908. Sensing electrodes 910, 912 are coupled with or disposed in the sensing material 908 and are connected with the substrate 902 in the illustrated embodiment. The sensing electrodes 910, 912 are conductive bodies that are conductively coupled with one or more processors 914 ("Impedance analyzer" in FIG. 8) that include one or more microprocessors, field programmable gate arrays, and/or integrated circuits. The processors 914 examine the impedance response of the sensing material 908 in order to determine the presence and/or amount of one or more hydrocarbons in the environment to which the sensing material 908 is exposed, as described herein.

Figure 5:
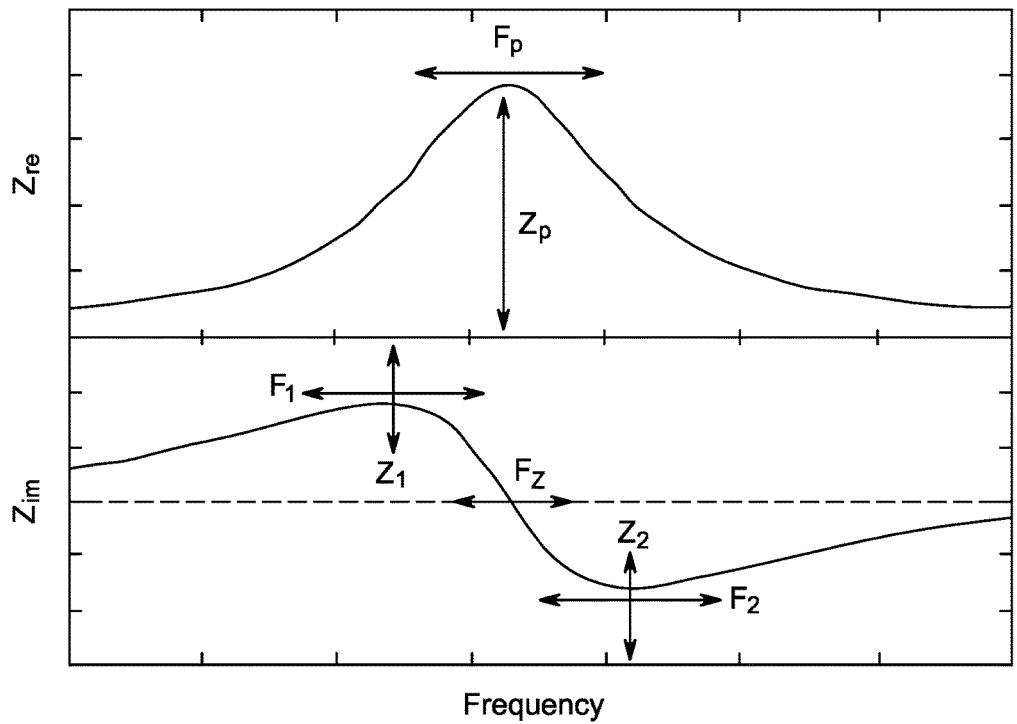
FIG. 5 depicts a graph of measured resonant impedance parameters of an embodiment of the resonant sensor.

FIG. 5 depicts a graph of measured resonant impedance parameters of an embodiment of the sensor, in accordance with embodiments of the present technique. The properties include the frequency of the maximum of the real part of the resonant impedance ($F_p$, resonance peak position), magnitude of the real part of the resonant impedance ($Z_p$, peak height), zero-reactance frequency ($F_z$, frequency at which the imaginary portion of resonant impedance may be zero), resonant frequency of the imaginary part of the resonant impedance ($F_1$), and anti-resonant frequency of the imaginary part of the resonant impedance ($F_2$), signal magnitude ($Z_1$) at the resonant frequency of the imaginary part of the resonant impedance ($F_1$), and signal magnitude ($Z_2$) at the anti-resonant frequency of the imaginary part of the resonant impedance ($F_2$). Other parameters may be measured using the entire resonant impedance spectra, for example, quality factor of resonance, phase angle, and magnitude of resonant impedance.

In contrast to operation of some known sensors, one or more embodiments of the inventive subject matter described herein are used to measure impedance responses of fluids, such as a hydrocarbon-based fuel, but at or under different operating conditions than what is currently used. The different operating conditions unexpectedly provide the sensing system with the ability to generate data used to differentiate between closely related gases using a single sensor. When a metal oxide semiconductor material is used in the sensor for gas sensing, and the sensor is operated under slightly relaxed operation conditions than prescribed (e.g., by the manufacturer of the sensor), the semiconductor material gives the ability for the sensor to quantitate different hydrocarbons.

For example, one or more of the sensors described herein may be operated by applying a heater voltage of less than the prescribed five volts. This results in a smaller electric field generated through the fluidic sample between the electrodes of the sensor and/or the area between the electrodes being at a lower temperature (e.g., relative to the greater heater voltage and temperature prescribed by many manufacturers of similar sensors). In one embodiment, the heater voltage is no more than four volts. This reduced heater voltage normally would be expected to result in a reduced response of the sensor to the constituents in the fluid sample. The sensor is then used to acquire impedance spectra of the response of the sensor to the fluid sample, as described above.

Figure 6:
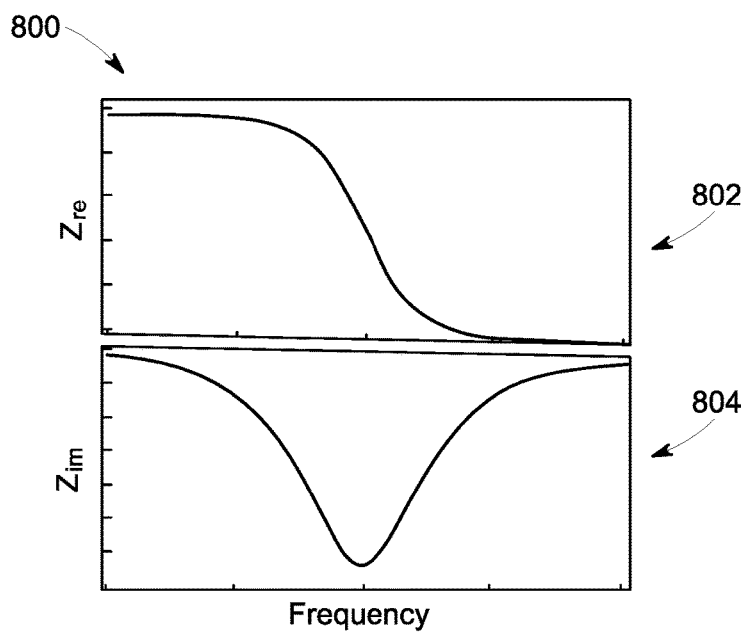
FIG. 6 illustrates a graphical illustration of measured responses corresponding to a real and imaginary impedance responses of the non-resonant sensor described herein in accordance with one embodiment.

FIG. 6 illustrates a graphical illustration of measured responses 800 corresponding to a real and imaginary impedance responses 802, 804 of the sensors described herein in accordance with one embodiment. For example, the impedance response 800 can represent the impedance sensor response of the sensor 114, 900 configured as a non-resonant sensor based on a stimulation waveform generated by the circuitry 116. The impedance responses 800 are measured by the circuitry 116 based on a measurement signal. For example, the circuitry 116 may receive the measurement signal from the electrodes 910, 912 in contact with the sensing material 908. The measurement signal is an electrical signal generated by the sensing material 908 in response to the stimulation waveform and the ambient environment to which the sensing material 908 is exposed. The measurement signal is representative of the impedance response of the sensing material 908. For example, the measurement signal may have electrical characteristics (e.g., voltage, current, frequency, and/or the like), which may be utilized by the circuitry 114 to calculate the impedance responses 800. The impedance responses 800 are divided into real portions 802 corresponding to the real impedance, Zre(f) of the impedance responses 800, and imaginary portions 804 of an imaginary impedance, Zim(f).

Figure 7:
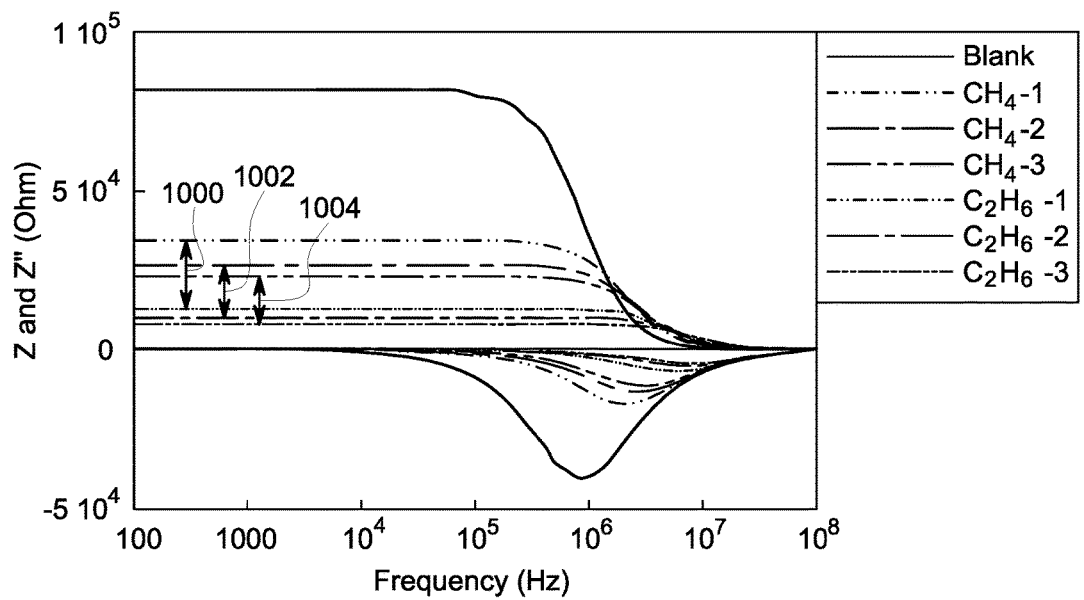
FIG. 7 illustrates impedance spectra of one or more embodiments of the sensor described herein using a heater voltage of at least approximately 20% less than the prescribed heater voltage.
Figure 8:
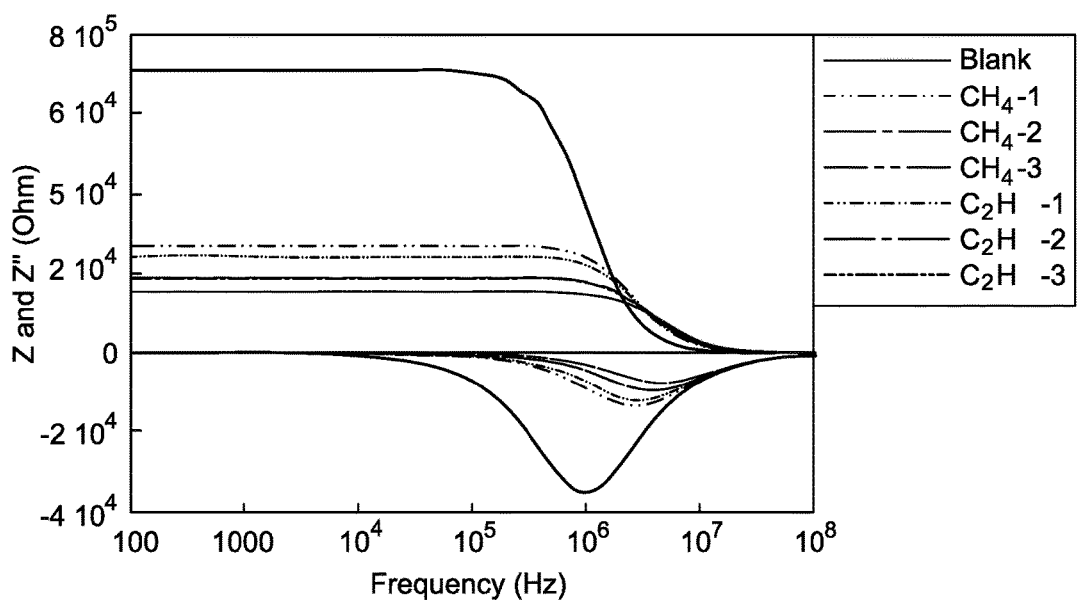
FIG. 8 illustrates impedance spectra of one or more embodiments of the sensor described herein using a heater voltage of five volts according to one example.

FIG. 7 illustrates impedance spectra of one or more embodiments of the sensors described herein using a heater voltage of at least approximately 20% less than the prescribed heater voltage. For example, the heater voltage may be four volts. FIG. 7 illustrates impedance spectra of one or more embodiments of the sensors described herein using a greater heater voltage of five volts according to one example. The impedance spectra of FIGS. 7 and 8 are shown alongside horizontal axes representative of different frequencies at which the fluid sample was probed by the sensor. The impedance spectra also are shown alongside vertical axes representative of different components of the resonant impedance of the fluid sample. For example, the vertical axes can indicate the real (Z) and imaginary (Z') parts of the resonant impedance of the sensor in the fluid. The real parts of the resonant impedance spectra are located above the zero value along the vertical axes and the imaginary parts of the resonant impedance spectra are located below the zero value along the vertical axes.

The impedance spectra shown in FIGS. 7 and 8 include the impedance spectra of a fluid (e.g., natural gas) having no measurable amount (e.g., in ppm) of methane or ethane ("Blank" in FIGS. 7 and 8), the impedance spectra of a fluid (e.g., natural gas) having 56 ppm of methane ("CH4–1" in FIGS. 7 and 8), the impedance spectra of a fluid (e.g., natural gas) having 112 ppm of methane ("CH4–2" in FIGS. 7 and 8), the impedance spectra of a fluid (e.g., natural gas) having 169 ppm of methane ("CH4–3" in FIGS. 7 and 8), the impedance spectra of a fluid (e.g., natural gas) having 56 ppm of ethane ("C2H6–1" in FIGS. 7 and 8), the impedance spectra of a fluid (e.g., natural gas) having 112 ppm of ethane ("C2H6 –2" in FIGS. 7 and 8), and the impedance spectra of a fluid (e.g., natural gas) having 169 ppm of ethane ("C2H6–3" in FIGS. 7 and 8).

As shown by a comparison of the impedance spectra shown in FIGS. 7 and 8, using a heater voltage in the sensor of four volts instead of five volts increases the differences between the impedance spectra for methane and ethane for all concentrations that were examined. In FIG. 8, the real parts of the impedance spectra for 56 ppm of methane and ethane are very close to each other over the entire range of examined frequencies, as are the imaginary parts of these impedance spectra. Additionally, the real parts of the impedance spectra for 112 ppm of methane and ethane overlap each other (e.g., are coextensive) over the entire range of examined frequencies, as do the imaginary parts of these impedance spectra. The same is true for the real parts and the imaginary parts of the impedance spectra for 169 ppm of methane and ethane. Consequently, use of the prescribed heater current of five volts may not be useful in differentiating between methane and ethane in a fluid such as natural gas.

In contrast, the impedance spectra shown in FIG. 7 clearly differentiate between methane and ethane. For example, the real parts of the impedance spectra for 56 ppm of methane and ethane are separated by a large difference 1000 (relative to the difference between the real parts of the impedance spectra for 56 ppm of methane and ethane using a heater voltage of five volts). The real parts of the impedance spectra for 112 ppm of methane and ethane are separated by a large difference 1002 (relative to the difference between the real parts of the impedance spectra for 112 ppm of methane and ethane using a heater voltage of five volts). Additionally, the real parts of the impedance spectra for 169 ppm of methane and ethane are separated by a large difference 1004 (relative to the difference between the real parts of the impedance spectra for 169 ppm of methane and ethane using a heater voltage of five volts).

The imaginary parts of the impedance spectra of methane and ethane using a heater voltage of four volts also are differentiated from each other by larger amounts relative to using the larger heater voltage. As shown in FIG. 7, the imaginary parts of the impedance spectra for methane and ethane do not overlap for the different concentrations over the entire range or substantially all of the entire range of frequencies, in contrast to the imaginary parts of the impedance spectra measured using a heater voltage of five volts.

Changing the heater voltage of the sensor is, however, not without risk. Operating the sensor at too low of a heater voltage can result in the sensor not responding to (and therefore not generating an output signal indicative of) the fluid (e.g., gas) of interest. Conversely, operating the sensor at too great of a heater voltage can significantly decrease the useful life of the sensor, as well as prevent or inhibit the sensor from detecting certain fluids of interest (e.g., differentiating between methane and ethane). One or more of the inventors have discovered that reducing the heater voltage from the prescribed, recommended, or industry-accepted value of five volts to four volts results in the sensor unexpectedly producing impedance spectra that allow for relatively easy differentiation between at least methane and ethane.

Optionally, the frequency at which the sensor is excited may be changed (in addition to or as an alternate to reducing the heater voltage) to determine the presence and/or concentration of one or more hydrocarbons in the fluid under examination.

Figure 9:
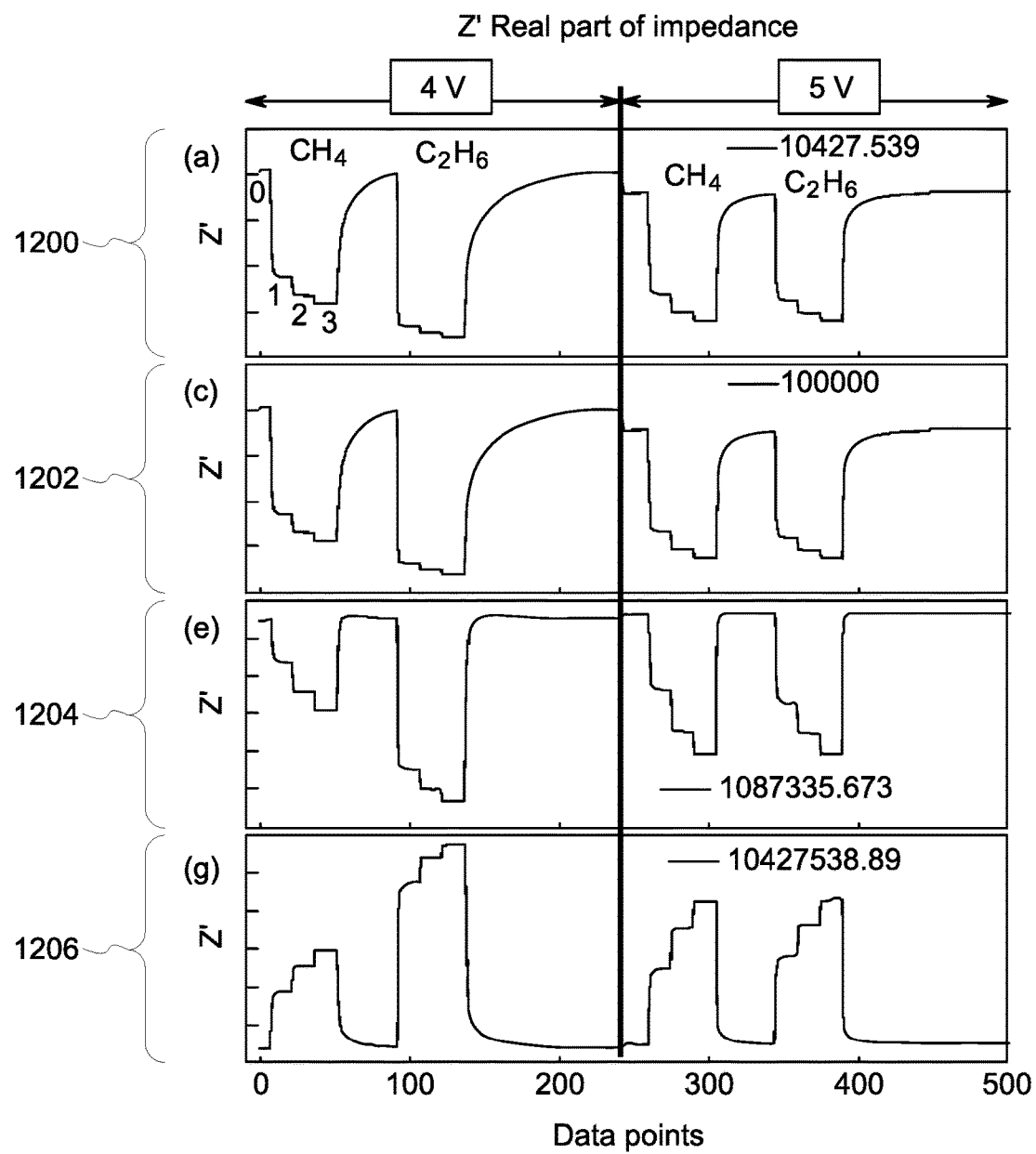
FIG. 9 illustrates several sets of real part of impedance spectra of methane and ethane using heater voltages of four volts or five volts, according to one example.

FIG. 9 illustrates several sets 1200, 1202, 1204, 1206 of real parts of impedance spectra of methane and ethane using heater voltages of four volts or five volts, according to one example. Each set 1200, 1202, 1204, 1206 includes the real part of the impedance spectra for methane and ethane for four volts (left side of each set 1200, 1202, 1204, 1206 in FIG. 9) and five volts (right side of each set 1200, 1202, 1204, 1206 in FIG. 9).

Figure 10:
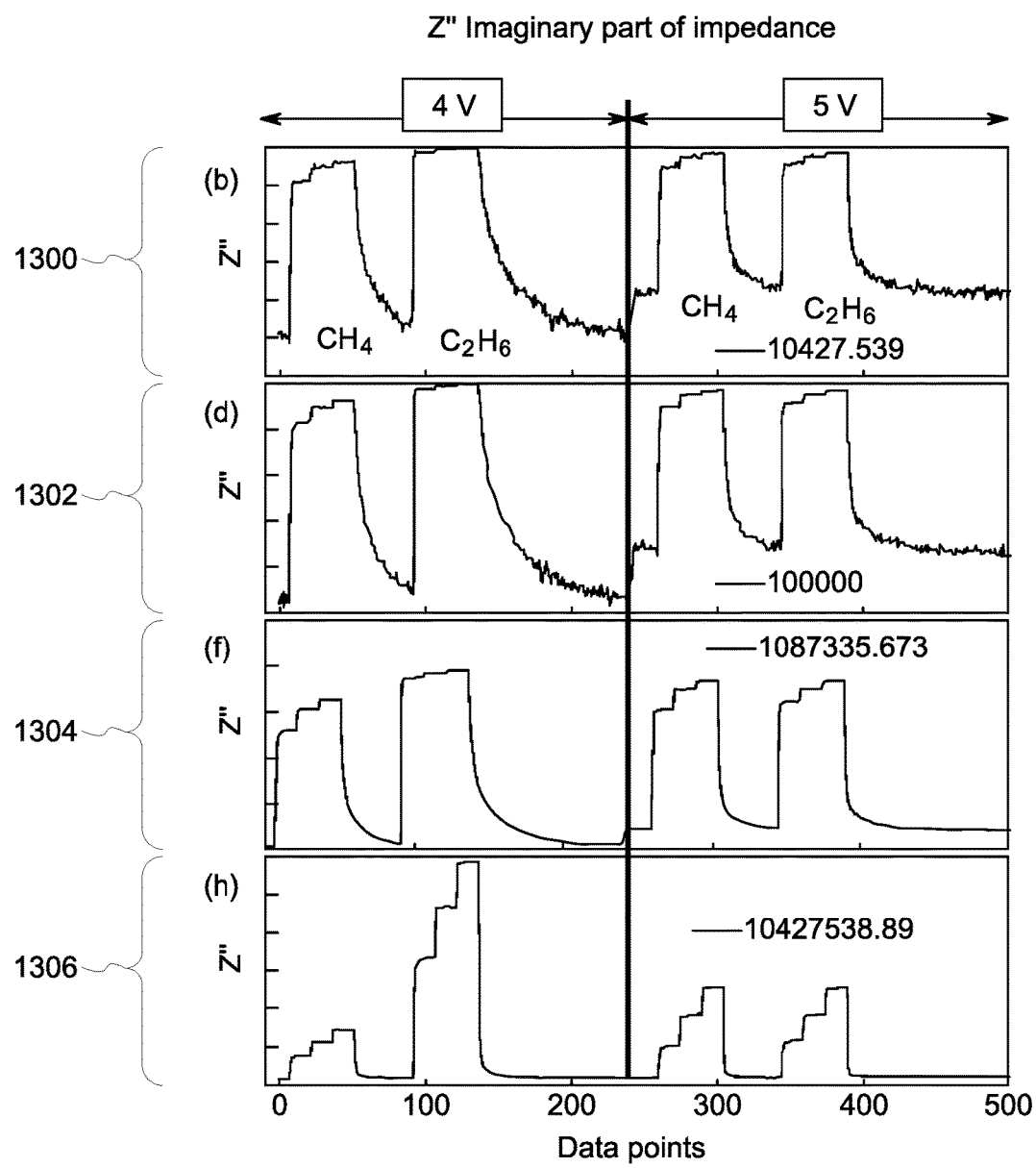
FIG. 10 illustrates several sets of imaginary part of impedance spectra of methane and ethane using heater voltages of four volts or five volts, according to one example.

FIG. 10 illustrates several sets 1300, 1302, 1304, 1306 of imaginary parts of impedance spectra of methane and ethane using heater voltages of four volts or five volts, according to one example. Each set 1300, 1302, 1304, 1306 includes the real part of the impedance spectra for methane and ethane for four volts (left side of each set 1300, 1302, 1304, 1306 in FIG. 10) and five volts (right side of each set 1300, 1302, 1304, 1306 in FIG. 10).

Each set of impedance spectra in FIG. 9 and in FIG. 10 was obtained at a different frequency of the RC circuit of the sensor. The sets 1200, 1300 were obtained at a frequency of approximately 10,427 Hz, the sets 1202, 1302 were obtained at a frequency of 100,000 Hz, the sets 1204, 1304 were obtained at a frequency of approximately 1,087,335 Hz, and the sets 1206, 1306 were obtained at a frequency of approximately 10,427,538 Hz.

As shown in FIGS. 9 and 10, the responses of the sensor to methane and ethane at a heater voltage of four volts and frequencies of approximately 10,427 Hz and 100,000 Hz are highly nonlinear. Conversely, the responses of the sensor to methane and ethane at the same heater voltage of four volts and frequencies of approximately 1,087,335 Hz and 10,427, 538 Hz are more linear (relative to the other frequencies).

The results shown in FIGS. 9 and 10 demonstrate that operating the sensor at the reduced heater voltage of four volts and at the higher frequencies (in the frequency range of 1 million to 10 million Hertz) results in differences between the impedance spectra for methane and ethane being greater. For example, the impedance spectra for methane at these operating conditions is significantly different from the impedance spectra for ethane at these same operating conditions.

Figure 11:
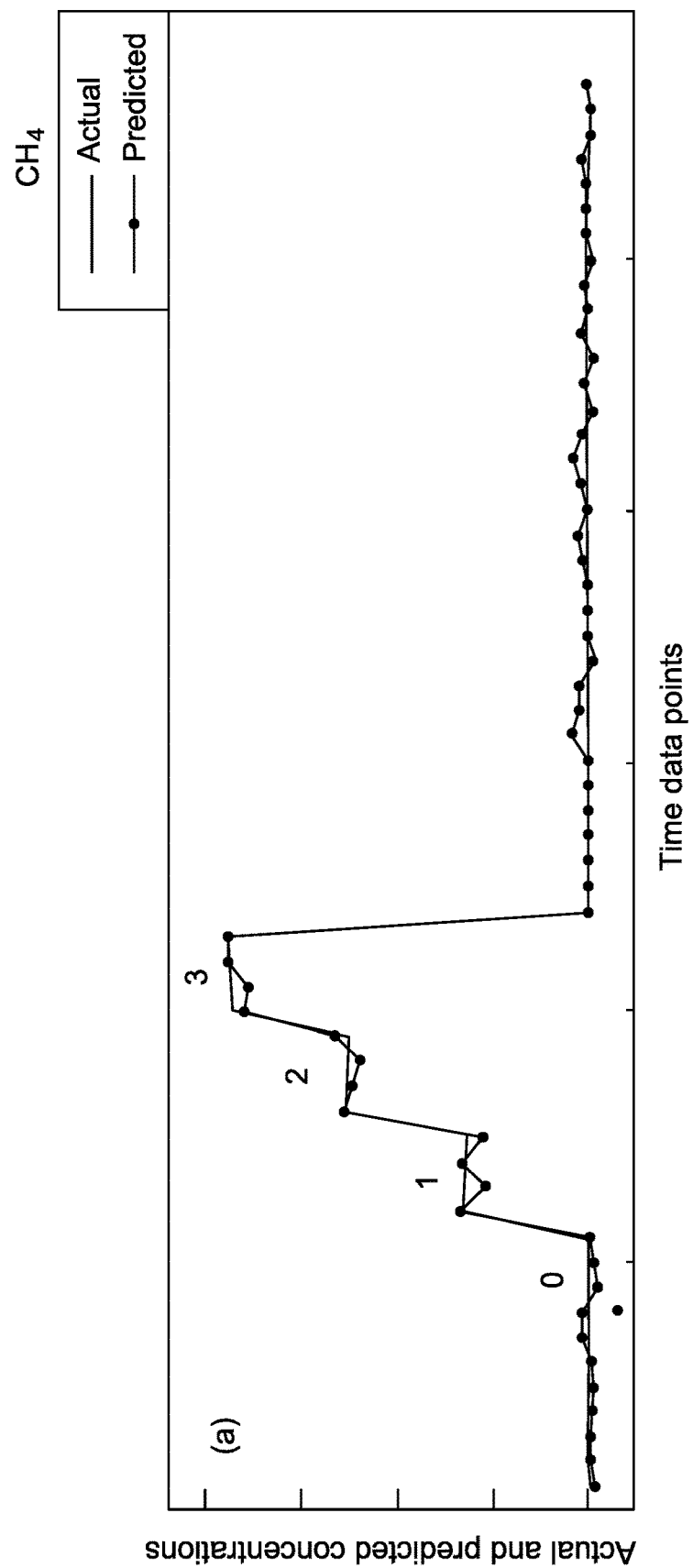
FIG. 11 illustrates the impedance spectra for independent quantitation of the sensor to only methane when the sensor has the response to both methane and ethane according to one example.
Figure 12:
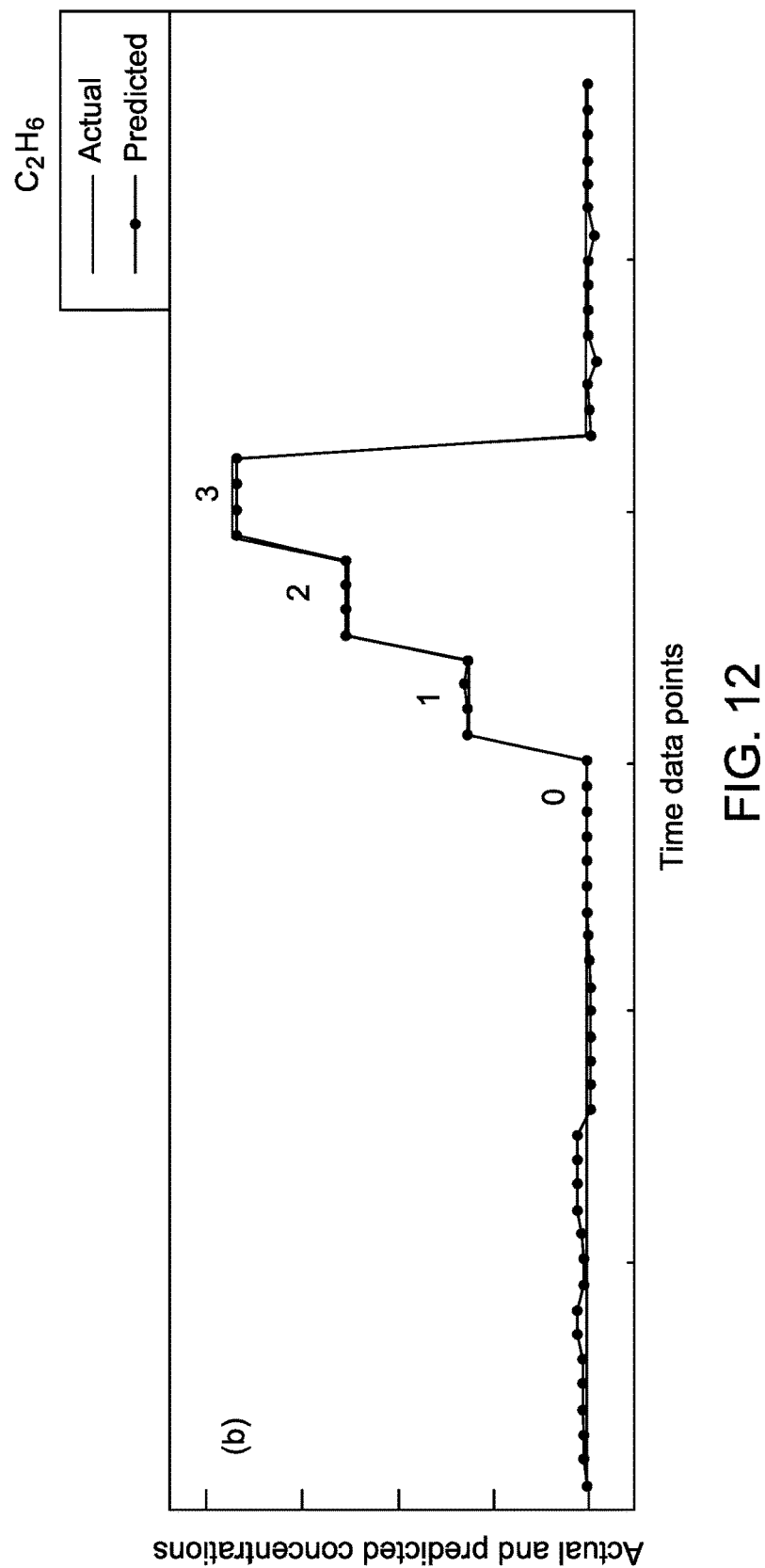
FIG. 12 illustrates the impedance spectra for independent quantitation of the sensor to only ethane when the sensor has the response to both methane and ethane according to one example.

When a conventional resistance sensor is sequentially exposed to closely related hydrocarbons, for example methane and ethane, it cannot discriminate methane and ethane and cannot separately quantify methane and ethane, as shown in FIG. 1. In contrast, FIG. 11 illustrates independent quantitation of only methane by the impedance sensor when the sensor is sequentially exposed to methane and ethane according to one example. FIG. 12 illustrates independent quantitation of only ethane by the impedance sensor when the sensor is sequentially exposed to methane and ethane according to one example. Such discrimination between closely related hydrocarbons and their independent quantitation was achieved when excitation heater conditions of the sensor were selected to be ~20% below the nominal prescribed value and were at a single level of operating voltage and at a single level of operating temperature. The dynamic profiles of the calibrated sensor response shown in FIGS. 11 and 12 were obtained using a DFSS Process Tool of a Six Sigma Toolbox of General Electric Company. For this quantitation of methane or ethane, responses of a single impedance sensor operating at a heater voltage of four volts and several frequencies were entered into the DFSS Process Tool along with known concentrations of methane and ethane that were 0 parts per million (ppm), 56 ppm, 112 ppm, and 169 ppm, labeled as 0, 1, 2, and 3 in the responses in FIG. 11 and FIG. 12. The DFSS Process Tool computed transfer functions that selectivity predicted the individual concentrations of methane (during exposure of the sensor to sequentially methane and ethane) and the individual concentrations of ethane (during exposure of the sensor to sequentially methane and ethane).

As shown in FIG. 11, the predicted concentrations of methane by the impedance sensor ("Predicted" in FIG. 11) are not significantly affected by the strong raw sensor response to both ethane and methane (where examples of raw sensor response are depicted in FIG. 9 and FIG. 10). The sensor can accurately predict methane concentrations using a developed transfer function for methane, as indicated by the close and many similarities between the predicted concentrations of methane and actual methane concentrations delivered to the impedance sensor ("Actual" in FIG. 11).

As shown in FIG. 12, the predicted concentrations of ethane by the impedance sensor ("Predicted" in FIG. 12) are not significantly affected by the strong raw sensor response to both ethane and methane (where examples of raw sensor response are depicted in FIG. 9 and FIG. 10). The sensor can accurately predict ethane concentrations, using a developed transfer function for ethane, as indicated by the close and many similarities between the predicted concentrations of ethane and actual ethane concentrations delivered to the impedance sensor ("Actual" in FIG. 12).

The data shown in FIGS. 11 and 12 indicate that the sensor can accurately predict concentrations of methane when the sensor is sequentially exposed to methane and ethane, yet also can accurately predict concentrations of ethane when the sensor is sequentially exposed to methane and ethane.

Figure 13:
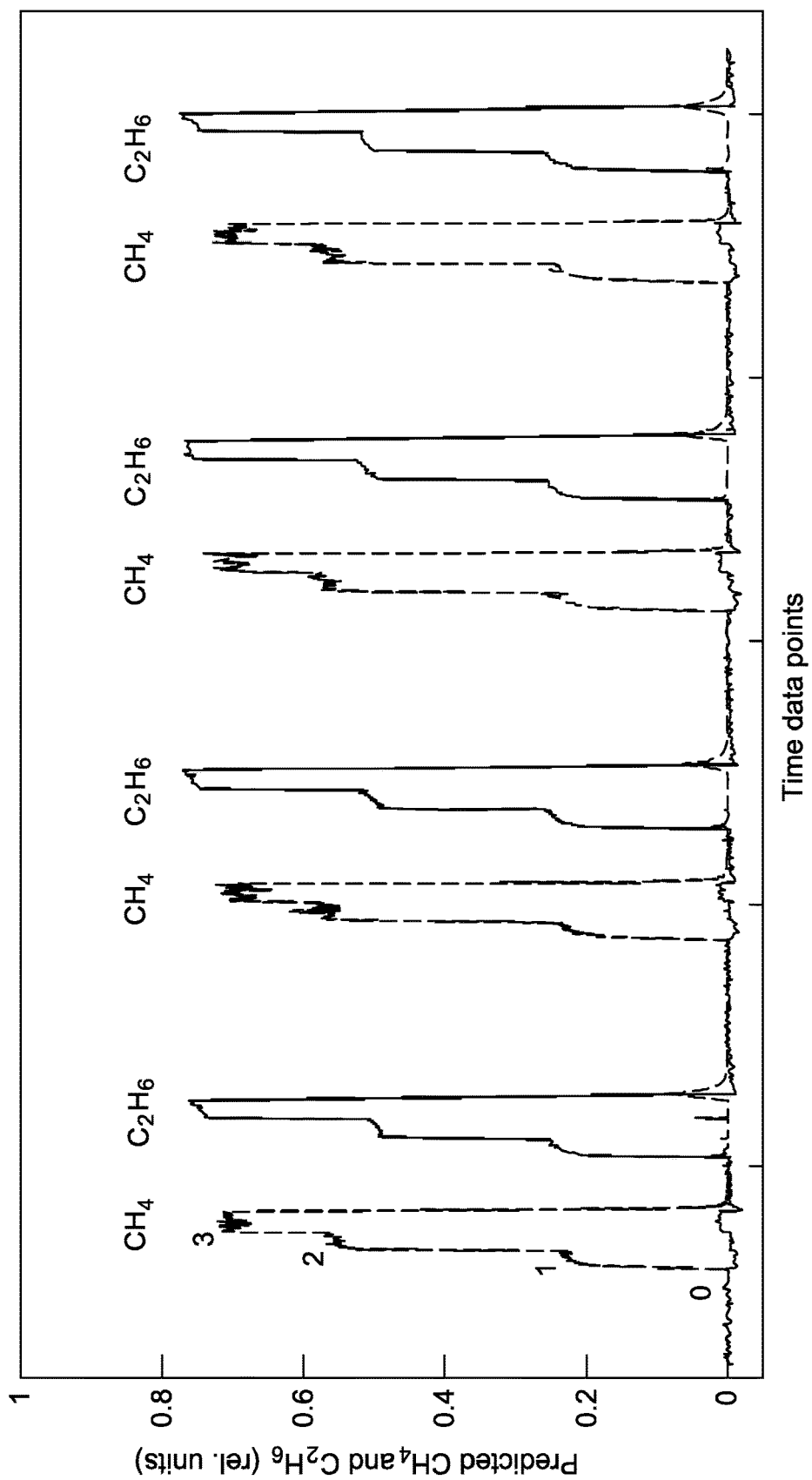
FIG. 13 illustrates independent quantitation of only methane and only ethane using developed transfer functions over multiple cycles of periodic exposures of the sensor to methane and ethane according to some examples.

FIG. 13 illustrates independent prediction of concentrations of only methane and only ethane using developed transfer functions over multiple cycles of periodic exposures of the sensor to methane and ethane according to some examples. The sensing material of the sensor can be exposed to only methane, only ethane, or a combination of methane, ethane, and optionally one or more additional hydrocarbons or other compounds, yet still be able to accurately measure amounts of methane, ethane, or other hydrocarbons. For example, with respect to the portions of the data shown in FIG. 13 that represent amounts of methane, the sensor may be exposed to ethane or methane, yet only output data on predicted type of gas and its concentration indicative of the amounts of methane. As another example, with respect to the portions of the data shown in FIG. 13 that represent amounts of ethane, the sensor may be exposed to ethane or methane, yet only output data on predicted type of gas and its concentration indicative of the amounts of ethane.

In one embodiment of the inventive subject matter described herein, it has been found that traditional resistance readout of metal oxide sensors under prescribed operation conditions (cell (a) in the Table below) does not provide selectivity of detection of methane and ethane. It was also found that impedance readout of metal oxide sensors under prescribed operation conditions (cell (b) in the Table below) also does not provide selectivity of detection of methane and ethane. Further, it was found that traditional resistance readout of metal oxide sensors under non-prescribed operation conditions (cell (c) in the Table below) does not provide selectivity of detection of methane and ethane. In contrast, selectivity of detection of methane and ethane was obtained only by using impedance measurements when performed under non-prescribed operation conditions for the sensor (cell (d) in the Table below). As a result, only a certain non-obvious combination of data acquisition conditions and relaxed operation conditions provided such as unexpected result of a significant importance.

| Cells | Operation conditions | Measurement mode | Selectivity of detection of methane vs ethane |
| --- | --- | --- | --- |
| (a) | Prescribed | Conventional resistance | No |
| (b) | Prescribed | Impedance | No |
| (c) | Non-prescribed | Conventional resistance | No |
| (d) | Non-prescribed | Impedance | Yes |

Figure 14:
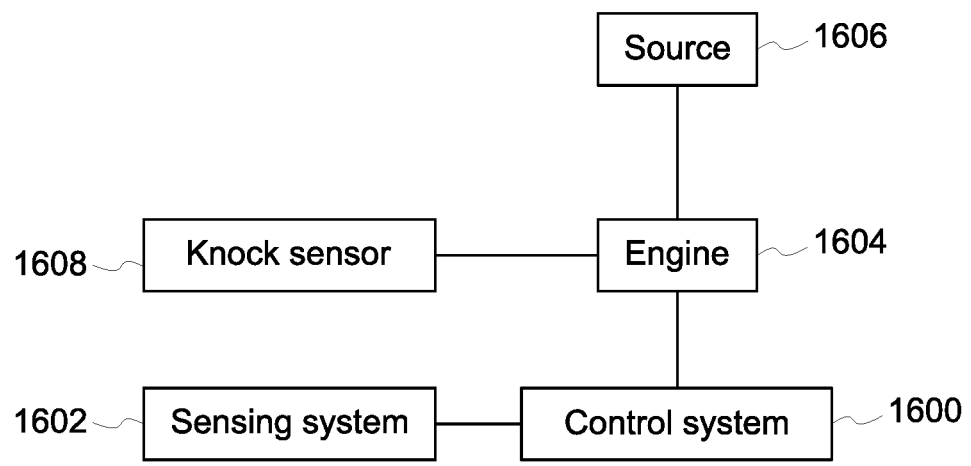
FIG. 14 illustrates one example of a control system.

One or more embodiments of the sensors and sensor systems described herein can be used in a variety of control systems that monitor and optionally control operation of other powered systems. FIG. 14 illustrates one example of such an engine control system 1600. The control system 1600 optionally can be referred to as an engine control unit, or ECU. The control system 1600 includes hardware circuitry that includes and/or is connected with one or more processors (e.g., microprocessors, field programmable gate arrays, integrated circuits, etc.) that control flow of two or more different fuels to an engine 1604 of a powered system, such as a vehicle, a power generator, or the like.

The engine 1604 is a dual fuel reciprocating internal combustion compression-ignition (RIC-CI) engine. The engine 1604 operates by the combination of conventional diesel fuel and natural gas, such as a mixture of CH4, C2H6, and small traces of other heavier hydrocarbons, and uses diesel fuel as the source of ignition. The engine 1604 can be designed to run on 100% diesel (DSL) fuel at any time during operation and natural gas (NGS) substitutes for the diesel fuel. This can result in various substitution rates of NGS:DSL. Some such substitution rates can range from 50% to 99%. If another engine (e.g., a conventional diesel engine designed for diesel-only operation) is converted or modified to operate on dual fuel, uncontrolled combustion or knocking can limit the substitution rate. The physics of combustion is the primary limiting factor on the substitution rate. The quality of the NGS supplied to the engine is a secondary limiting factor. NGS comprised of pure CH4 defines an upper limit or maximum (e.g., combustion-physics dictated) substitution rate. If the NGS includes heavier hydrocarbons such as ethane (C2H6), the level or percentage or ppm of C2H6 in CH4 will determine the practical knock-free substitution rate for the engine. Physics-based modeling along with engine tests can be used to determine the substitution rate as a function of CH4 content in the NGS. Based on the engine modeling and tests, the map of CH4 content versus engine speed and load, and NGS is loaded/stored in the engine controller.

The control system 1600 can communicate with one or more embodiments of the sensing systems or sensors 1602 ("Sensing System" in FIG. 14) to determine the amount of CH4 content in the NGS and/or to modify operation of the engine 1604 based on the amount of CH4 content in the NGS.

The CH4 content in the NGS can be dependent on a source 1606 of the gas, which can be piped gas from utility providers, oil well, gas well, etc. Optionally, the source 1606 may be a tank holding compressed and/or liquefied natural gas as fuel for the engine 1604. The sensing system 1602 includes one or more hydrocarbon sensors (as described above), which provides CH4 content information (e.g., measurements of the amount of CH4) to the control system 1600, thereby enabling the control system to define or limit the amount of NGS supplied to the engine 1604 based on one or more engine operating conditions (speed, load, etc.) using or by reading from a pre-set NGS calibration that is loaded on to the control system 1600.

In another embodiment, the hydrocarbon sensor 1600 is applied or used in conjunction with a knock sensor 1608. The knock sensor 1608 provides data indicative of knocking or an absence of knocking by the engine 1604 to the control system 1600. In the event of incipient or an earliest indication of engine operation under knocking conditions, the amount of gas supplied (via a substitution rate of NGS) can be significantly cut-back or reduced by the control system 1600 or, in an extreme case, the control system 1600 can stop the flow of NGS (resulting in 100% diesel only operation of the engine 1604). This can eliminate or reduce the amount of knocking within the engine 1604.

As another example, the sensing system is used to discriminate between different types of emissions of one or more gases such as biogenic gas emissions and thermogenic gas emissions. For example, the sensing system is disposed at one or more locations (e.g., near a gas-production well) and measures gas emissions present near the gas well. The gas well may be positioned in a remote location near a wetland or any other source of decaying vegetation or near a livestock farm as depicted in FIG. 15.

Figure 15:
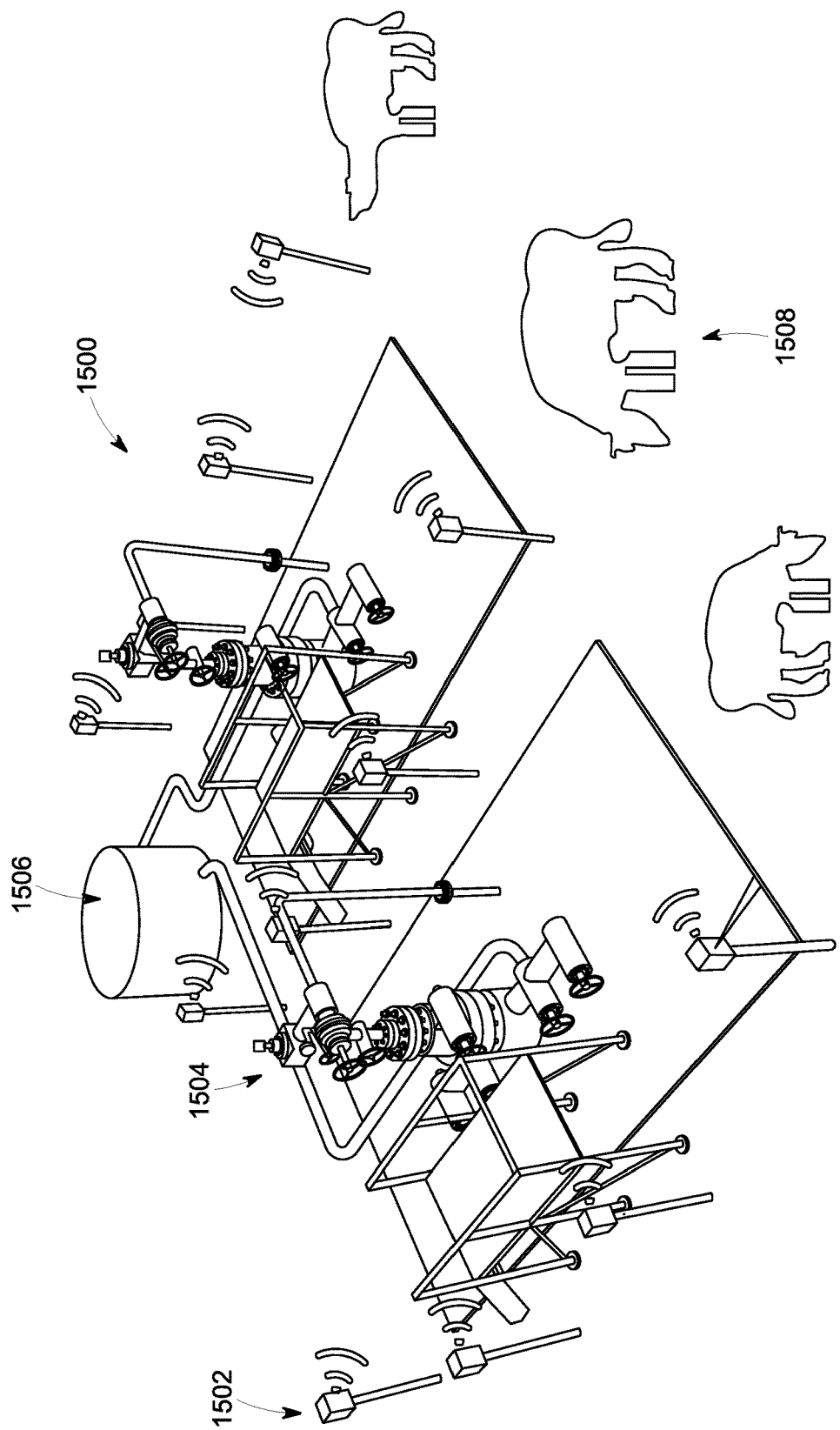
FIG. 15 illustrates one or more embodiments a sensing system for measurements of biogenic gas emissions and thermogenic gas emissions according to one example.

FIG. 15 illustrates one or more embodiments a sensing system 1500 for measurements of biogenic gas emissions and thermogenic gas emissions according to one example. The sensing system 1500 includes sensors 1502 disposed around or near sources of biogenic gas emissions and/or thermogenic gas emissions, such as gas production wells 1504, storage tanks 1506 for storage of the gas from the wells 1504, livestock 1508, etc. The sensors 1502 may represent one or more embodiments of the sensors described herein.

The sensor system 1500 is positioned for measurements of biogenic gas emissions and thermogenic gas emissions. Thus, the deployed sensing system may detect both, biogenic gas emissions and thermogenic gas emissions. Biogenic gas emissions are created by methanogenic organisms in wetlands, rain forests, landfills, and other sources of decaying vegetation as well as in the gastrointestinal systems of ruminant livestock (including cows, buffalo, goats, sheep, bison, and others). Thermogenic gas emissions are created from buried organic materials such as fossil fuels that are naturally produced at greater temperature and pressure as compared to biogenic gas. The ratio of concentrations of methane to ethane in thermogenic emissions is much less than the ratio of concentrations of methane to ethane in biogenic emissions. Thus, the ratio of concentrations of methane to ethane measured by the sensing system indicates whether the detected emission is from a biogenic source or from a thermogenic source. For example, a larger measured ratio of concentrations of methane to ethane is an indication of a biogenic emission.

Yet another embodiment of the sensing system is that the sensing system can be used to detect accumulation of vaporized fuel (e.g., in the form of unburned hydrocarbons) in an enclosure such as engine cab of a locomotive or engine room of a marine vessel or indoor fuel storage area. Detecting these conditions and providing a warning and/or fuel supply shut-off could be used in a system to prevent thermal incidents or fires. For example, the control system automatically closes one or more valves in response to the sensing system measuring at least a designated amount or concentration of a flammable hydrocarbon. This can increase safety within the area or enclosure in which the sensing system is deployed.

Figures 16, 17:
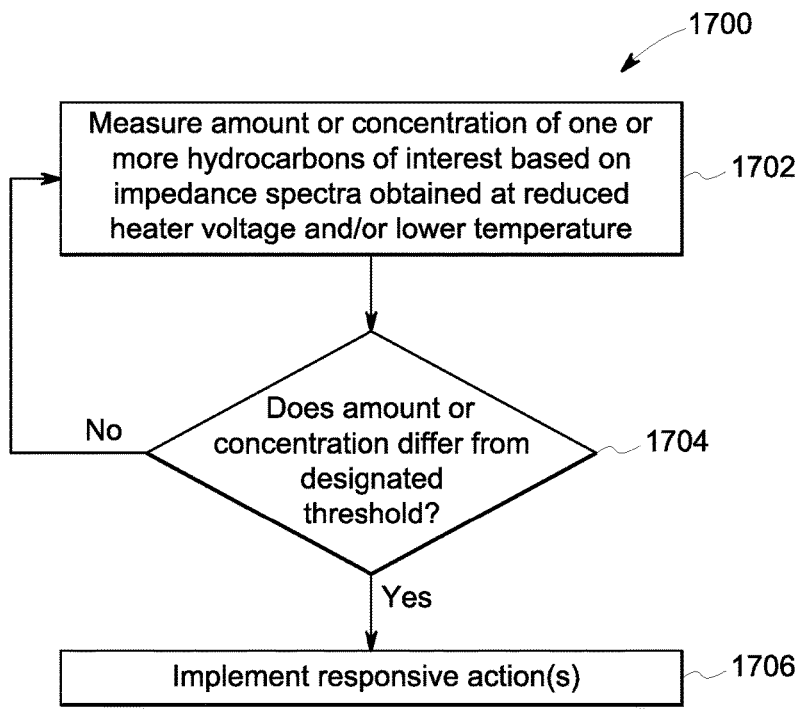
FIG. 16 illustrates a flowchart of one embodiment of a method for sensing one or more hydrocarbons of interest.
FIG. 17 illustrates a powered system according to one embodiment.

FIG. 16 illustrates a flowchart of one embodiment of a method 1700 for sensing one or more hydrocarbons of interest. The method 1700 is performed by one or more embodiments of the sensing systems or sensors described herein in one embodiment. At 1702, an amount or concentration of one or more hydrocarbons of interest is measured. The hydrocarbon or hydrocarbons of interest include hydrocarbons having lower weight (e.g., molecular weight) than one or more other hydrocarbons in one embodiment. For example, a hydrocarbon of interest may be methane while a hydrocarbon other than the hydrocarbon of interest may be ethane in a fuel, such as natural gas. The amount and/or concentration of the hydrocarbon(s) of interest are measured by one or more embodiments of the sensing systems or sensors described herein at operational condition(s) that are different than known, prescribed conditions. For example, the sensor can operate at a reduced heater voltage of four volts (instead of five volts or greater) and/or can heat the sensing film exposed to the sample being examined (e.g., the natural gas) to a lower temperature of less than 300 degrees Celsius. The amount and/or concentration of the hydrocarbon(s) of interest are determined from one or more impedance spectra, as described above.

At 1704, a determination is made as to whether the measured concentration and/or amount of the hydrocarbon(s) of interest differs from one or more designated thresholds. For example, if the measured amount of methane in natural gas is lower than a designated threshold, then the flow of the natural gas to an engine may need to be interrupted or stopped to avoid reducing operational efficiency of the engine. As another example, if the measured amount of ethane in natural gas is greater than a designated threshold, then the flow of the natural gas to the engine may need to be interrupted or stopped to avoid uncontrolled/undesired rate of combustion or knock, and protect the engine from reduced operational efficiency and damage to critical engine components and sub-systems.

As another example, if the amount of one or more gases in the oil of a transformer exceeds a designated threshold, then the transformer may be deactivated (e.g., by stopping the conduction of current to the transformer). As another example, if the amount of methane sensed near a well exceeds a designated threshold, then the methane may indicate a thermogenic emission of the methane from the well. As another example, if the amount of vaporized fuel exceeds a designated threshold, then the amount of the fuel can indicate that there is a dangerous amount of vaporized fuel in the area.

If the amount and/or concentration of the hydrocarbon of interest differs from a designated threshold (e.g., exceeds a larger, upper designated threshold or falls below a smaller, lower designated threshold), then flow of the method 1700 can proceed toward 1706. Otherwise, flow of the method 1700 may return toward 1702 to continue measuring the amount and/or concentration of the hydrocarbon(s) of interest, or may terminate.

At 1706, one or more responsive actions are implemented. For example, if the measured amount of methane in natural gas is lower than a designated threshold, then the flow of the natural gas to an engine is automatically terminated and/or the flow of another fuel (e.g., diesel fuel) to the engine is automatically commenced. As another example, if the amount of one or more gases in the oil of a transformer exceeds a designated threshold, then the transformer is automatically deactivated. As another example, if the amount of methane sensed near a well exceeds a designated threshold, then the well or a pump associated with the well is automatically deactivated. As another example, if the amount of vaporized fuel exceeds a designated threshold, then the flow of fuel is automatically terminated and/or a warning is issued to warn one or more persons near the vaporized fuel to leave the area.

In one embodiment, the sensor can operate at an increased heater voltage as compared to the nominal prescribed operating heater voltage and/or can heat the sensing film exposed to the sample being examined to a higher temperature as compared to the nominal prescribed operating temperature. Such increased heater voltage and/or temperature of the sensing film can be selected to be ~20% above the nominal prescribed values. In one embodiment, the sensor can operate at a heater voltage that is different as compared to the nominal prescribed operating heater voltage and/or can heat the sensing film exposed to the sample being examined to a temperature that is different as compared to the nominal prescribed operating temperature. These differences may be the increased or decreased voltage of the heater and/or the increased or decreased temperature of the sensing film. Such different heater voltage and/or temperature of the sensing film can be selected to be ~20% different from the nominal prescribed values. In another embodiment, such different heater voltage and/or temperature of the sensing film can be selected to be in the range from ~10% to ~80% different from the nominal prescribed values. In one embodiment, the voltage of the heater is maintained at a constant voltage and the temperature of the sensing film is maintained at a constant temperature. In another embodiment, the voltage of the heater is maintained at a variable voltage and the temperature of the sensing film is maintained at a variable temperature.

FIG. 17 illustrates a powered system 1800 according to one embodiment. The powered system 1800 is a ground-based vehicle in FIG. 17, but optionally may be another type of powered system or vehicle, such as a marine vessel, an engine room, etc. The powered system 1800 includes an engine (not shown in FIG. 17) and a hydrocarbon sensor 1804 that measures the presence and/or amount of one or more hydrocarbons within an enclosed space or volume 1802 of the powered system 1800. In one embodiment, the enclosed space or volume 1802 is an operator cab of a vehicle, an engine room, an indoor storage space for fuel, etc. The sensor 1804 can represent one or more of the sensors or sensing systems described herein.

The sensor 1804 operates to sense the presence and/or amount of one or more hydrocarbons in the enclosed space or volume 1802 of the powered system 1800, such as methane, ethane, or the like. The detected presence of the hydrocarbon(s) and/or measured amounts of the hydrocarbon(s) that exceed one or more designated limits can indicate an unsafe or increasingly unsafe situation, such as a situation where the hydrocarbon(s) in the enclosed space or volume 1802 may be in danger of combusting. A sensing system onboard the powered system 1800 can include the sensor 1804 and a controller 1806, where the sensor 1804 communicates the detected presence and/or amount of the hydrocarbon(s) to the controller 1806. The controller 1806 represents hardware circuitry that includes and/or is connected with one or more processors (e.g., one or more microprocessors, field programmable gate arrays, and/or integrated circuits) that receive output from the sensor 1804 that indicates the presence and/or amount of the hydrocarbon(s) in the space or volume 1802. In response to receiving this output (e.g., the presence of the hydrocarbon(s) and/or a measured amount of the hydrocarbon(s) that exceeds a designated upper limit), the controller 1806 generates a control signal that is communicated to an output device 1808, such as a display device, speaker, or the like. The control signal directs the output device 1808 to visually and/or audibly present a warning to one or more persons located in the enclosed space or volume 1802. This can allow for the persons to exit the space or volume 1802 before the hydrocarbon(s) combust.

In one embodiment, a system includes an impedance gas sensor configured to be in contact with one or more hydrocarbons. The impedance sensor includes electrodes and a sensing region circuit that is configured to have a sensing material and to generate electrical stimuli to the sensing material upon exposure to one or more hydrocarbons at one or more of a reduced heater voltage or a reduced sensing region temperature as compared to a prescribed heater voltage or a prescribed sensing region temperature. The system also includes one or more processors configured to receive electrical signals from the sensor, where the electrical signals are representative of impedance responses of the sensing material to one or more hydrocarbons. The one or more processors also are configured to analyze the impedance responses and determine an amount of at least one hydrocarbon of interest in the one or more hydrocarbons.

In one example, the sensing material is metal oxide.

In one example, the sensing material is a semiconducting material.

In one example, the impedance sensor is resonant impedance sensor.

In one example, the impedance sensor is non-resonant impedance sensor.

In one example, the impedance sensor is configured to generate the electrical stimuli to the sensing material upon exposure to one or more hydrocarbons at the reduced temperature of less than three hundred degrees Celsius.

In one example, the impedance sensor is configured to generate the electrical stimuli to the sensing material upon exposure to one or more hydrocarbons at a temperature reduced by at least approximately 20% from a nominal prescribed temperature.

In one example, the impedance sensor is configured to generate the electrical stimuli to the sensing material upon exposure to one or more hydrocarbons at a temperature different by at least approximately 20% from a nominal prescribed temperature.

In one example, the impedance sensor is configured to apply the electrical stimuli to the sensing material upon exposure to one or more hydrocarbons at the reduced temperature that is maintained at a constant temperature.

In one example, the impedance sensor is configured to generate the electrical generate the electrical stimuli to the sensing material upon exposure to one or more hydrocarbons at an excitation frequency greater than 10,000 hertz.

In one example, the one or more processors are configured to change a substitution rate of a first fuel for a different, second fuel supplied to an engine based on the impedance responses of the gas sensor.

In one example, the one or more processors are configured to change the substitution rate by controlling a flow of the natural gas to the engine.

In one example, the one or more processors are configured to discriminate between biogenic and thermogenic emissions of methane based on the ratio of measured methane concentration to measured ethane concentration.

In one embodiment, a method includes placing an impedance gas sensor in contact with one or more hydrocarbons, applying (using a sensing region circuit and across electrodes of the impedance sensor) electrical stimuli to the sensing material upon exposure to one or more hydrocarbons at a reduced heater temperature, and analyzing electrical signals from the impedance sensor that are representative of impedance responses of the sensor to the electrical stimuli. The impedance responses are analyzed to determine an amount of a hydrocarbon of interest in the one or more hydrocarbons.

In one example, the electrical stimuli are applied to the sensing material at the reduced temperature of less than three hundred degrees Celsius.

In one example, the electrical stimuli are applied to the sensing material at the reduced temperature that is maintained at a constant temperature.

In one example, the electrical stimuli are applied to the sensing material at an excitation frequency greater than 10,000 hertz.

In one example, the electrical stimuli are applied to the sensing material upon exposure to one or more hydrocarbons with a temperature of the sensing material that is different by at least approximately 20% from a nominal prescribed temperature.

In one example, the method also includes changing a substitution rate of a first fuel for a different, second fuel supplied to an engine based on the impedance responses.

In one example, the substitution rate by controlling a flow of the natural gas to the engine.

In one example, the method also includes discriminating between biogenic and thermogenic emissions of methane for the safe and environmentally clean operation of gas-production facilities based on the ratio of measured methane concentration to measured ethane concentration.

In one embodiment, a system includes an impedance sensor having a sensing film configured to be in contact with a fuel flowing to a dual fuel engine. The impedance sensor includes electrodes and a sensing region circuit that is configured to generate electrical stimuli across the sensing film. The system also includes one or more processors configured to receive electrical signals from the impedance sensor. The electrical signals are representative of impedance responses of the sensing film to the electrical stimuli. The one or more processors also are configured to analyze the impedance response and determine an amount of one or more of methane or ethane in the fuel based on the impedance responses.

In one example, the one or more processors are configured to control the impedance sensor to generate the electrical stimuli at a heater voltage reduced by at least approximately 20% from a nominal prescribed voltage.

In one example, the one or more processors are configured to control the impedance sensor to generate the electrical stimuli to heat the sensing material at a temperature reduced by at least approximately 20% from a nominal prescribed temperature.

In one example, the one or more processors are configured to change the fuel flowing to the dual fuel engine from natural gas to diesel fuel responsive to the amount of ethane in the fuel increasing above a designated threshold.

In one example, the impedance sensor is resonant impedance sensor.

In one example, the impedance sensor is non-resonant impedance sensor.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain- English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. A system comprising:
   an impedance sensor having a sensing film configured to be in contact with a fuel flowing to a dual fuel engine, the impedance sensor including electrodes and a sensing region circuit that is configured to generate electrical stimuli across the sensing film; and
   one or more processors configured to receive electrical signals from the impedance sensor, the electrical signals representative of impedance responses of the sensing film to the electrical stimuli, the one or more processors configured to analyze the impedance response and determine an amount of one or more of methane or ethane in the fuel based on the impedance responses.

2. The system of claim 1, wherein the one or more processors are configured to control the impedance sensor to generate the electrical stimuli at a heater voltage reduced by at least approximately 20% from a nominal prescribed voltage.

3. The system of claim 1, wherein the one or more processors are configured to control the impedance sensor to generate the electrical stimuli to heat the sensing material at a temperature reduced by at least approximately 20% from a nominal prescribed temperature.

4. The system of claim 1, wherein the one or more processors are configured to change the fuel flowing to the dual fuel engine from natural gas to diesel fuel responsive to the amount of ethane in the fuel increasing above a designated threshold.

5. The system of claim 1, wherein the impedance sensor is resonant impedance sensor.

6. The system of claim 1, wherein the impedance sensor is non-resonant impedance sensor.

7. A system comprising:
   an impedance gas sensor configured to be in contact with one or more hydrocarbons, the impedance sensor including electrodes and a sensing region circuit that is configured to have a sensing material and to generate electrical stimuli to the sensing material upon exposure to one or more hydrocarbons at one or more of a reduced heater voltage or a reduced sensing region temperature as compared to a prescribed heater voltage or a prescribed sensing region temperature; and
   one or more processors configured to receive electrical signals from the sensor, the electrical signals representative of impedance responses of the sensing material to one or more hydrocarbons, the one or more processors configured to analyze the impedance responses and determine an amount of at least one hydrocarbon of interest in the one or more hydrocarbons.

8. The system of claim 7, wherein the sensing material is metal oxide.

9. The system of claim 7, wherein the sensing material is a semiconducting material.

10. The system of claim 7, wherein the impedance sensor is resonant impedance sensor.

11. The system of claim 7, wherein the impedance sensor is non-resonant impedance sensor.

12. The system of claim 7, wherein the impedance sensor is configured to generate the electrical stimuli to the sensing material upon exposure to one or more hydrocarbons at the reduced temperature of less than three hundred degrees Celsius.

13. The system of claim 7, wherein the impedance sensor is configured to generate the electrical stimuli to the sensing material upon exposure to one or more hydrocarbons at a temperature reduced by at least approximately 20% from a nominal prescribed temperature.

14. The system of claim 7, wherein the impedance sensor is configured to generate the electrical stimuli to the sensing material upon exposure to one or more hydrocarbons at a temperature different by at least approximately 20% from a nominal prescribed temperature.

15. The system of claim 7, wherein the impedance sensor is configured to apply the electrical stimuli to the sensing material upon exposure to one or more hydrocarbons at the reduced temperature that is maintained at a constant temperature.

16. The system of claim 7, wherein the impedance sensor is configured to generate the electrical generate the electrical stimuli to the sensing material upon exposure to one or more hydrocarbons at an excitation frequency greater than 10,000 hertz.

17. The system of claim 7, wherein the one or more processors are configured to change a substitution rate of a first fuel for a different, second fuel supplied to an engine based on the impedance responses of the gas sensor.

18. The system of claim 17, wherein the one or more processors are configured to change the substitution rate by controlling a flow of the natural gas to the engine.

19. The system of claim 7, wherein the one or more processors are configured to discriminate between biogenic and thermogenic emissions of methane based on the ratio of measured methane concentration to measured ethane concentration.

20. A method comprising:
   placing an impedance gas sensor in contact with one or more hydrocarbons;
   applying, using a sensing region circuit and across electrodes of the impedance sensor, electrical stimuli to the sensing material upon exposure to one or more hydrocarbons at a reduced heater temperature; and
   analyzing electrical signals from the impedance sensor that are representative of impedance responses of the sensor to the electrical stimuli, the impedance responses analyzed to determine an amount of a hydrocarbon of interest in the one or more hydrocarbons.

21. The method of claim 20, wherein the electrical stimuli are applied to the sensing material at the reduced temperature of less than three hundred degrees Celsius.

22. The method of claim 20, wherein the electrical stimuli are applied to the sensing material at the reduced temperature that is maintained at a constant temperature.

23. The method of claim 20, wherein the electrical stimuli are applied to the sensing material at an excitation frequency greater than 10,000 hertz.

24. The method of claim 20, wherein the electrical stimuli are applied to the sensing material upon exposure to one or more hydrocarbons with a temperature of the sensing material that is different by at least approximately 20% from a nominal prescribed temperature.

25. The method of claim 20, further comprising changing a substitution rate of a first fuel for a different, second fuel supplied to an engine based on the impedance responses.

26. The method of claim 25, wherein the substitution rate by controlling a flow of the natural gas to the engine.

27. The method of claim 20, further comprising discriminating between biogenic and thermogenic emissions of methane for the safe and environmentally clean operation of gas-production facilities based on the ratio of measured methane concentration to measured ethane concentration.

\* \* \* \* \*